United States Patent
DaSilva et al.

(10) Patent No.: US 10,932,819 B2
(45) Date of Patent: Mar. 2, 2021

(54) UTERINE MANIPULATORS AND RELATED COMPONENTS AND METHODS

(71) Applicant: CooperSurgical, Inc., Trumbull, CT (US)

(72) Inventors: Rodrigo DaSilva, Waterbury, CT (US); Daniel Giardina, New Fairfield, CT (US)

(73) Assignee: CooperSurgical, Inc., Trumbull, CT (US)

( * ) Notice: Subject to any disclaimer, the term of this patent is extended or adjusted under 35 U.S.C. 154(b) by 220 days.

(21) Appl. No.: 15/956,180

(22) Filed: Apr. 18, 2018

(65) Prior Publication Data

US 2019/0321079 A1   Oct. 24, 2019

(51) Int. Cl.

| A61B 17/42 | (2006.01) |
|---|---|
| A61B 1/303 | (2006.01) |
| A61B 1/06 | (2006.01) |
| A61B 17/00 | (2006.01) |
| A61B 17/32 | (2006.01) |

(52) U.S. Cl.
CPC .......... *A61B 17/4241* (2013.01); *A61B 1/303* (2013.01); *A61B 1/0676* (2013.01); *A61B 2017/00557* (2013.01); *A61B 2017/320052* (2013.01); *A61B 2017/4225* (2013.01)

(58) Field of Classification Search
CPC ............... A61B 17/42; A61B 17/4241; A61B 2017/4216–4233
See application file for complete search history.

(56) References Cited

U.S. PATENT DOCUMENTS

| 1,856,295 A | 5/1932 | Sovatkin |
|---|---|---|
| 2,186,143 A | 1/1940 | Neugass |

(Continued)

FOREIGN PATENT DOCUMENTS

| CN | 207186648 | 4/2018 | ............ A61B 17/02 |
|---|---|---|---|
| DE | 20110921 | 12/2001 | ............ A61B 17/42 |

(Continued)

OTHER PUBLICATIONS

Gunatillake, Pathiraja A., et al. "Polyurethane Elastomers with Low Modulus and Hardness Based on Novel Copolyether Macrodiols." Wiley Online Library, John Wiley & Sons, Ltd, Dec. 7, 1998, onlinelibrary.wiley.com/doi/epdf/10.1002/(SICI)1097-4628(Mar. 7, 1997) 63:10<1373::AID-APP18>3.0.CO;2-5.*

(Continued)

*Primary Examiner* — Tan-Uyen T Ho
*Assistant Examiner* — Charles M Wei
(74) *Attorney, Agent, or Firm* — Fish & Richardson P.C.

(57) ABSTRACT

A method of positioning a uterine manipulator within a patient includes applying a deforming force to a colpotomizer cup of the uterine manipulator to adjust the colpotomizer cup from a nominal width configuration to a reduced width configuration, inserting the colpotomizer cup into a vaginal canal of the patient while the colpotomizer cup is in the reduced width configuration, removing the deforming force from the colpotomizer cup to allow the colpotomizer cup to expand from the reduced width configuration to the nominal width configuration, and positioning the colpotomizer cup about a cervix of the patient while the colpotomizer cup is in the nominal width configuration.

19 Claims, 14 Drawing Sheets

(56) References Cited

U.S. PATENT DOCUMENTS

| | | | |
|---|---|---|---|
| 2,456,806 A | 12/1948 | Wolffe | |
| 2,744,708 A | 5/1956 | Bedford, Jr. | |
| 3,096,764 A | 7/1963 | Hiebert | |
| 3,131,690 A | 5/1964 | Innis et al. | |
| 3,153,267 A | 10/1964 | Rowland, Jr. | |
| 3,196,865 A | 7/1965 | Rose | |
| 3,749,088 A | 7/1973 | Kohlmann | |
| 3,766,909 A | 10/1973 | Ozbey | |
| 3,769,983 A | 11/1973 | Merav | |
| 3,877,433 A | 4/1975 | Librach | |
| 3,878,848 A | 4/1975 | Hiebert | |
| 3,948,270 A | 4/1976 | Hasson | |
| 4,022,208 A | 5/1977 | Valtchev | |
| 4,066,071 A | 1/1978 | Nagel | |
| 4,323,057 A | 4/1982 | Jamieson | |
| 4,379,457 A | 4/1983 | Gravener et al. | |
| 4,430,076 A | 2/1984 | Harris | |
| 4,533,349 A | 8/1985 | Bark | |
| 4,562,832 A | 1/1986 | Wilder et al. | |
| 4,597,030 A | 6/1986 | Brody et al. | |
| 4,627,421 A | 12/1986 | Symbas et al. | |
| 4,719,925 A | 1/1988 | Parsons | |
| 4,775,362 A | 10/1988 | Kronner | |
| 4,807,625 A | 2/1989 | Singleton | |
| 4,823,167 A | 4/1989 | Manska et al. | |
| 4,981,355 A | 1/1991 | Higgins | |
| 4,996,974 A | 3/1991 | Ciarlei | |
| 4,997,419 A | 3/1991 | Lakatos et al. | |
| 5,037,430 A | 8/1991 | Hasson | |
| 5,059,198 A | 10/1991 | Gimpelson | |
| 5,104,377 A | 4/1992 | Levine | |
| 5,174,276 A | 12/1992 | Crockard | |
| 5,181,842 A | 1/1993 | Sunderland et al. | |
| 5,209,754 A | 5/1993 | Ahluwalia | |
| 5,232,443 A | 8/1993 | Leach | |
| 5,237,985 A | 8/1993 | Hodgson et al. | |
| 5,242,240 A | 9/1993 | Gorham | |
| 5,259,836 A | 11/1993 | Thurmond et al. | |
| 5,273,026 A | 12/1993 | Wilk | |
| 5,338,297 A | 8/1994 | Kocur et al. | |
| 5,353,784 A | 10/1994 | Nady-Mohamed | |
| 5,409,496 A | 4/1995 | Rowden et al. | |
| 5,431,662 A | 7/1995 | Nicholas | |
| 5,520,698 A * | 5/1996 | Koh | A61B 17/4241 128/898 |
| 5,540,700 A | 7/1996 | Rowden et al. | |
| 5,549,563 A | 8/1996 | Kronner | |
| 5,571,115 A | 11/1996 | Nicholas | |
| 5,624,399 A | 4/1997 | Ackerman | |
| 5,643,285 A * | 7/1997 | Rowden | A61B 17/4241 606/119 |
| 5,690,617 A | 11/1997 | Wright | |
| 5,810,806 A | 9/1998 | Ritchart et al. | |
| 5,835,657 A | 11/1998 | Suarez et al. | |
| 5,840,077 A * | 11/1998 | Rowden | A61B 17/4241 606/119 |
| 5,928,249 A * | 7/1999 | Saadat | A61B 17/42 604/19 |
| 6,068,121 A | 5/2000 | McGlinch | |
| 6,080,118 A | 6/2000 | Blythe | |
| 6,159,170 A | 12/2000 | Borodulin et al. | |
| 6,328,729 B1 | 12/2001 | Jervis | |
| 6,348,036 B1 | 2/2002 | Looney et al. | |
| 6,423,075 B1 | 7/2002 | Singh et al. | |
| 6,651,992 B1 | 11/2003 | Smith | |
| 6,682,100 B2 | 1/2004 | Wood et al. | |
| 6,741,895 B1 | 5/2004 | Gafni et al. | |
| 6,752,819 B1 | 6/2004 | Brady et al. | |
| 6,932,759 B2 | 8/2005 | Kammerer et al. | |
| 7,052,453 B2 | 5/2006 | Presthus et al. | |
| 7,334,503 B1 | 2/2008 | Newman | |
| 8,545,513 B2 | 10/2013 | Blair et al. | |
| 8,740,916 B2 | 6/2014 | Blair et al. | |
| 8,939,988 B2 | 1/2015 | Auerbach et al. | |
| 9,636,144 B2 * | 5/2017 | Parys | A61B 90/39 |
| 9,649,130 B2 | 5/2017 | Parys | |
| 9,743,956 B2 | 8/2017 | Parys et al. | |
| 9,788,859 B2 | 10/2017 | Parys | |
| 2001/0021854 A1 | 9/2001 | Donnez et al. | |
| 2003/0073951 A1 * | 4/2003 | Morton | A61B 10/0041 604/73 |
| 2003/0187334 A1 | 10/2003 | Biswas | |
| 2003/0195386 A1 | 10/2003 | Thierfeld et al. | |
| 2003/0220538 A1 | 11/2003 | Jacquetin | |
| 2004/0122462 A1 | 6/2004 | Bakos et al. | |
| 2004/0138528 A1 | 7/2004 | Richter et al. | |
| 2004/0193043 A1 | 9/2004 | Duchon et al. | |
| 2004/0230092 A1 | 11/2004 | Thierfeld et al. | |
| 2005/0065395 A1 | 3/2005 | Mellier | |
| 2005/0085827 A1 | 4/2005 | G. et al. | |
| 2005/0107818 A1 | 5/2005 | Valtchev | |
| 2005/0184124 A1 | 8/2005 | Scirica et al. | |
| 2005/0277948 A1 * | 12/2005 | Cedars | A61B 17/42 606/119 |
| 2006/0015001 A1 | 1/2006 | Staskin et al. | |
| 2006/0199994 A1 | 9/2006 | Inman et al. | |
| 2006/0241652 A1 | 10/2006 | Doll et al. | |
| 2007/0088351 A1 | 4/2007 | Ewaschuk et al. | |
| 2007/0129615 A1 | 6/2007 | Backman et al. | |
| 2007/0135679 A1 | 6/2007 | Hunt et al. | |
| 2008/0058833 A1 | 3/2008 | Rizvi | |
| 2008/0221590 A1 | 9/2008 | Ikeda et al. | |
| 2008/0243176 A1 | 10/2008 | Weitzner et al. | |
| 2008/0245371 A1 | 10/2008 | Gruber | |
| 2008/0249535 A1 | 10/2008 | Valtchev | |
| 2009/0131954 A1 | 5/2009 | Christian et al. | |
| 2010/0106163 A1 | 4/2010 | Blair et al. | |
| 2010/0152749 A1 | 6/2010 | Von Pechmann et al. | |
| 2010/0168784 A1 | 7/2010 | Pustilnik | |
| 2010/0179575 A1 | 7/2010 | Von Pechmann et al. | |
| 2010/0280309 A1 | 11/2010 | Von Pechmann | |
| 2010/0305578 A1 | 12/2010 | Auerbach et al. | |
| 2011/0130769 A1 | 6/2011 | Boebel et al. | |
| 2012/0109146 A1 | 5/2012 | Auerbach et al. | |
| 2012/0109147 A1 | 5/2012 | Auerbach et al. | |
| 2012/0323079 A1 | 12/2012 | Bakare et al. | |
| 2012/0330324 A1 | 12/2012 | Sauer | |
| 2013/0018386 A1 | 1/2013 | Ponder | |
| 2013/0085508 A1 | 4/2013 | Hess | |
| 2013/0131459 A1 * | 5/2013 | Williams | A61B 1/06 600/249 |
| 2013/0345714 A1 | 12/2013 | Blair et al. | |
| 2014/0276916 A1 | 9/2014 | Ahluwalia et al. | |
| 2014/0303641 A1 | 10/2014 | Boebel et al. | |
| 2014/0378751 A1 | 12/2014 | Buster et al. | |
| 2016/0100861 A1 * | 4/2016 | Parys | A61B 90/39 600/249 |
| 2016/0106463 A1 * | 4/2016 | Egle | A61B 17/42 606/119 |
| 2017/0325844 A1 * | 11/2017 | Prior | A61B 1/0676 |
| 2018/0014854 A1 * | 1/2018 | Souther | A61B 17/43 |
| 2018/0325554 A1 * | 11/2018 | Prior | A61B 17/4241 |

FOREIGN PATENT DOCUMENTS

| | | | |
|---|---|---|---|
| DE | 69532474 | 11/2004 | ............ A61B 17/42 |
| DE | 10341561 | 4/2005 | ............ A61B 17/00 |
| EP | 0400458 | 12/1990 | ............ A61B 1/30 |
| EP | 0890342 | 9/2003 | ............ A61B 17/42 |
| JP | 2016-515861 | 6/2016 | ............ A61B 90/00 |
| WO | WO 2008/074054 | 6/2008 | ............ A61B 1/303 |
| WO | WO 2009/078953 | 6/2009 | ............ A61F 2/00 |

OTHER PUBLICATIONS

The Extended European Search Report for European Application No. 19 170 083.0 dated Aug. 12, 2019.

Culligan et al., "Long-Term Success of Abdominal Sacral Colpopexy Using Synthetic Mesh," Am. J. Obstet. Gynecol., Dec. 2002.

"Koh Cup Vaginal Fornices Delineator & Colpo-Pneumo Occluder," *The Koh Colpotomizer™ System*, Directions for Use; 6 pages; Sep. 2008.

(56) References Cited

OTHER PUBLICATIONS

"Laparoscopic Hysterectomy and Colpotomy Accessories for Use Exclusively with the RUMI System Uterine Manipulator," *CooperSurgical The KOH Colpotomizer System*; 2 pages; Oct. 2006.
ConMed, VCare® Plus and VCare® DX Plus, Uterine Manipulators, http://www.conmed.com/en/medical-specialties/laparoscopic-robotic-and-open-surgery/gyn-and-gyn-oncology/instruments/uterine-manipulation/vcare-plus-and-vcare-dx, Web Page (2018).
The Notice of Reasons for Rejection issued by the Japanese Patent Office for Japanese Application No. JP 2019-077531, dated Sep. 9, 2020 (with English Translation).

* cited by examiner

UTERINE MANIPULATORS AND RELATED COMPONENTS AND METHODS

TECHNICAL FIELD

This disclosure relates to uterine manipulators and related components and methods.

BACKGROUND

Uterine manipulators are medical instruments that are used for manipulating (e.g., moving or repositioning) a patient's uterus during medical procedures. Such procedures include surgical procedures, such as laparoscopic gynecologic surgery (e.g., total laparoscopic hysterectomy (TLH) surgery). Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage the uterus. Generally, the distal portion of the instrument is advanced through the vaginal canal and into the uterus. With the distal portion inserted within a uterus, the uterus can be manipulated through surgeon-controlled or physician-controlled movements of the proximal portion. Following completion of a procedure, the instrument is removed from the patient's body via the vaginal canal.

SUMMARY

In general, this disclosure relates to uterine manipulators and related components and methods. Such uterine manipulators can be used for manipulating a patient's uterus during gynecological surgery and/or gynecological diagnostic procedures.

In one aspect, a method of positioning a uterine manipulator within a patient includes applying a deforming force to a colpotomizer cup of the uterine manipulator to adjust the colpotomizer cup from a nominal width configuration to a reduced width configuration, inserting the colpotomizer cup into a vaginal canal of the patient while the colpotomizer cup is in the reduced width configuration, removing the deforming force from the colpotomizer cup to allow the colpotomizer cup to expand from the reduced width configuration to the nominal width configuration, and positioning the colpotomizer cup about a cervix of the patient while the colpotomizer cup is in the nominal width configuration.

Embodiments may include one or more of the following features.

In some embodiments, inserting the colpotomizer cup into the vaginal canal of the patient includes moving the colpotomizer cup along a shaft of the uterine manipulator.

In certain embodiments, the method further includes locking the colpotomizer cup at a predetermined location along the shaft.

In some embodiments, the method further includes advancing the colpotomizer cup within the vaginal canal to the cervix of the patient while the colpotomizer cup is in the reduced width configuration.

In certain embodiments, applying the deforming force to the colpotomizer cup includes squeezing the colpotomizer cup.

In some embodiments, removing the deforming force from the colpotomizer cup includes releasing the colpotomizer cup.

In certain embodiments, applying the deforming force to the colpotomizer cup includes collapsing the colpotomizer cup.

In some embodiments, inserting the colpotomizer cup into the vaginal canal includes inserting the colpotomizer cup into a vaginal entryway of the patient.

In certain embodiments, the colpotomizer cup includes polyurethane.

In some embodiments, one or more materials from which the colpotomizer cup is formed have an elastic modulus in a range of about 5.5 MPa to about 171 MPa.

In certain embodiments, one or more materials from which the colpotomizer cup is formed have a hardness in a range of 85 Shore A to 100 Shore A.

In some embodiments, a wall thickness of the colpotomizer cup is in a range of about 0.2 cm to about 0.7 cm.

In certain embodiments, one or more materials from which the colpotomizer cup is formed have an elastic modulus in a range of about 5.5 MPa to about 171 MPa and a hardness in a range of 85 Shore A to 100 Shore A.

In some embodiments, the colpotomizer cup has a maximum internal diameter of about 2.5 cm, about 3.0 cm, about 3.5 cm, or about 4.0 cm.

In certain embodiments, the method further includes visualizing the cervix within the colpotomizer cup through one or more of multiple viewing windows of the colpotomizer cup.

In some embodiments, the multiple viewing windows extends about a majority of a circumference of the colpotomizer cup.

In another aspect, a uterine manipulator includes a deformable colpotomizer cup defining a receptacle sized to receive a cervix of a patient, wherein the deformable colpotomizer cup is adjustable from a nominal width configuration to a reduced width configuration for insertion of the colpotomizer cup into a vaginal canal of the patient, and wherein the deformable colpotomizer cup is adjustable from the reduced width configuration to the nominal width configuration for placement of the colpotomizer cup about the cervix.

Embodiments may include one or more of the following features.

In some embodiments, the colpotomizer cup includes polyurethane.

In certain embodiments, one or more materials from which the colpotomizer cup is formed have an elastic modulus in a range of about 5.5 MPa to about 171 MPa.

In some embodiments, one or more materials from which the colpotomizer cup is formed have a hardness in a range of 85 Shore A to 100 Shore A.

In certain embodiments, a wall thickness of the colpotomizer cup is in a range of about 0.2 cm to about 0.7 cm.

In some embodiments, one or more materials from which the colpotomizer cup is formed have an elastic modulus in a range of about 5.5 MPa to about 171 MPa and a hardness in a range of 85 Shore A to 100 Shore A.

In certain embodiments, the colpotomizer cup has a maximum internal diameter of about 2.5 cm, about 3.0 cm, about 3.5 cm, or about 4.0 cm.

Embodiments may provide one or more of the following advantages.

In some embodiments, the colpotomizer cup is formed of one or more materials that can reversibly deform (e.g., that can rebound from a reduced size configuration to a nominal size configuration) to allow flexible adjustment of the colpotomizer cup for insertion of the uterine manipulator into a patient. Such deformable materials have one or more properties that allow the colpotomizer cup to maintain its mechanical integrity upon application of typical forces that would be applied to the colpotomizer cup during a surgical procedure. For example, the colpotomizer cup can be squeezed into a collapsed, folded configuration to facilitate insertion of the colpotomizer cup into a vaginal entryway of a relatively small size. In some examples, such a reduced size configuration (e.g., reduced width configuration) of the colpotomizer cup can prevent the need for a user (e.g., a surgeon) to cut the vaginal wall near the vaginal entryway to enlarge the vaginal entryway for allowing insertion of an otherwise larger sized colpotomizer cup. The collapsed, folded configuration of the colpotomizer cup can also facilitate placement of the colpotomizer cup within the vaginal vault, which can be difficult to do in cases where the vaginal vault has thinned tissue that can be easily torn or lacerated.

In certain embodiments, the colpotomizer cup may be selectable from multiple predetermined sizes for use on patients with a range of vaginal and uterine anatomical feature sizes. In some embodiments, viewing windows of the colpotomizer cup extend about a majority of the circumference of the colpotomizer cup to optimize visibility of the base of the uterus contained therein during a surgical procedure.

Other aspects, features, and advantages will be apparent from the description, the drawings, and the claims.

DETAILED DESCRIPTION

Figure 1:
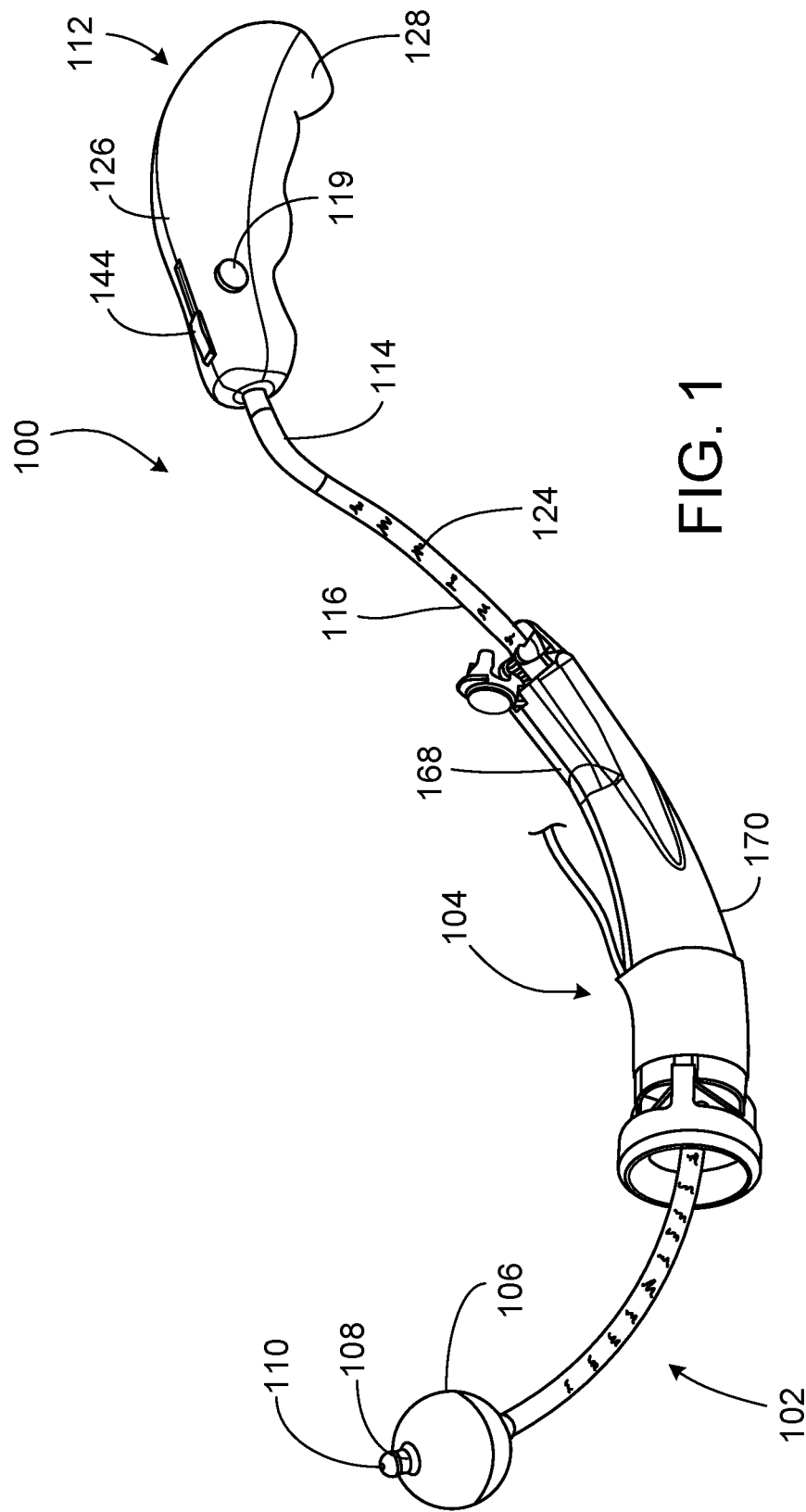
FIG. 1 is a perspective view of a uterine manipulator including a manipulator handle, a shaft, an expandable balloon, a light source, and a colpotomizer assembly.

FIG. 1 illustrates a uterine manipulator 100 adapted for insertion into a vaginal canal for use in female pelvic surgical procedures. The uterine manipulator 100 includes a shaft 102 configured to extend within a cervix for use in repositioning a uterus and a colpotomizer assembly 104 disposed about the shaft 102 and configured to receive the cervix. The uterine manipulator 100 further includes an expandable balloon 106 secured to a distal tip 108 of the shaft 102 and configured to maintain a position of the distal tip 108 within the uterus. A light source 110 is mounted to the distal tip 108 of the shaft 102 and can be used to illuminate the vaginal canal and external orifice of the uterus (i.e., the cervical os) during insertion of the uterine manipulator 100. A manipulator handle 112 is connected to a proximal portion 114 of the shaft 102.

Figure 2:
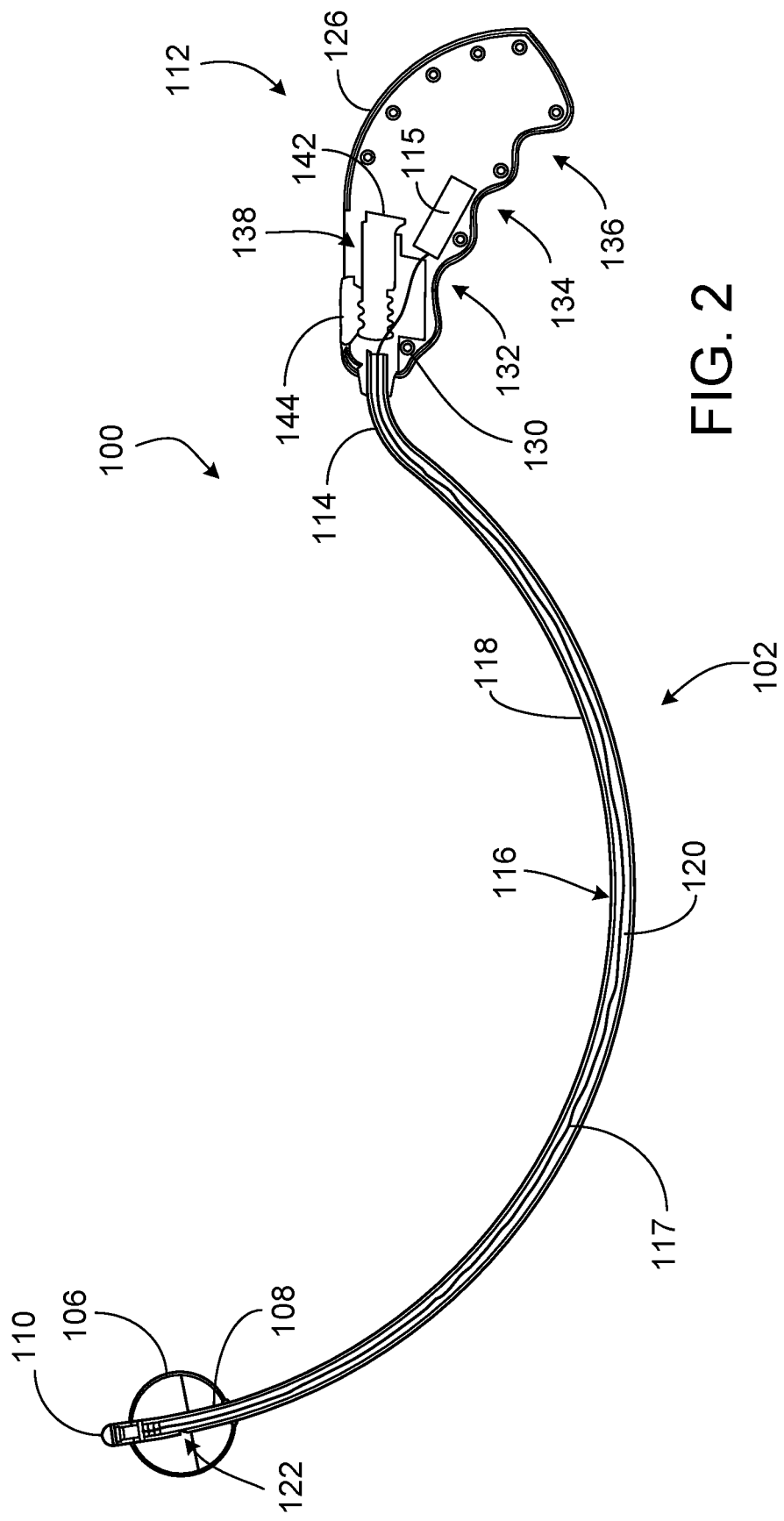
FIG. 2 is a cross-sectional side view of the uterine manipulator of FIG. 1, shown without the colpotomizer assembly.

Referring to FIG. 2, the shaft 102 of the uterine manipulator 100 is formed as a rigid cannula that has a generally curved (e.g., arcuate) shape. The shaft 102 includes the proximal portion 114 that extends into the manipulator handle 112, a central portion 116 along which the colpotomizer assembly 104 is displaceable for engaging the cervix, and the distal tip 108 configured to extend through the cervix and into the uterus. The central portion 116 and a section of the proximal portion 114 that extends distally from the manipulator handle 112 are covered by a shrink tube 118 that provides lubricity for sliding of the colpotomizer assembly 104 along the shaft 102 and traction for locking the colpotomizer assembly 104 in a desired position along the shaft 102, as will be discussed in more detail with respect to FIG. 4. The shrink tube 118 typically has a thickness of about 0.010 inch to about 0.020 inch (e.g., about 0.014 inch to about 0.018 inch).

The shaft 102 of the uterine manipulator 100 defines a central lumen 120 that allows passage of air between the manipulator handle 112 and the expandable balloon 106. The central lumen 120 of the shaft 102 also allows passage of one or more electrical wires 117 from a power source 115 (e.g., a battery) disposed within the manipulator handle 112 to the light source 110 secured to the distal tip 108 of the shaft 102. The shaft 102 also defines an opening 122 located along the distal tip 108 that allows passage of air between the central lumen 120 and the expandable balloon 106 for inflating and deflating the expandable balloon 106. The shaft 102 further includes a set of ruler markings 124 (shown in FIGS. 1 and 3) printed across the shrink tube 118 along the central portion 116 and that indicate a distance from the fundus of the uterus when the uterine manipulator 100 is appropriately, fully inserted into the uterus (e.g., when the distal tip 108 of the shaft 102 is positioned adjacent the fundus, as will be discussed in more detail with respect to FIG. 8). The ruler markings 124 may be provided in English units (e.g., inches) or S.I. units (e.g., mm or cm).

The shaft 102 (e.g., including the section of the proximal portion 114 extending from the manipulator handle 112, the central portion 116, and the distal tip 108) typically has a length of about 11.0 inches to about 12.0 inches (e.g., about 11.4 inches to about 11.7 inches. The section of the proximal portion 114 extending from the manipulator handle 112 typically has a radius of curvature of about 5.0 inches to about 7.0 inches (e.g., about 6.0 inches). The central portion 116 of the shaft 102 typically has a radius of curvature of about 5.50 inches to about 7.00 inches (e.g., about 6.00 inches to about 6.25 inches). The distal tip 108 of the shaft 102 typically has a length of about 0.50 inch to about 0.60 inch (e.g., about 0.55 inch to about 0.56 inch). The shaft 102 typically has an inner diameter of about 0.100 inch to about 0.150 inch (e.g., about 0.128 inch to about 0.134 inch) and a wall thickness of about 0.020 inch to about 0.040 inch (e.g., about 0.027 inch to about 0.029 inch).

The expandable balloon 106 is secured at opposite ends to the distal tip 108 of the shaft 102. The balloon 106 can be secured to the shaft 102 via chemical bonding and compressive capture via the shrink tube 118. The expandable balloon 106 surrounds the opening 122 along the distal tip 108 and accordingly is in fluid communication with the central lumen 120 of the shaft 102. The expandable balloon 106 can be rapidly inflated and rapidly deflated by syringe actuation that occurs at the manipulator handle 112. The expandable balloon 106 typically has a length of about 1.2 inches to about 1.8 inches (e.g., about 1.4 inches to about 1.6 inches). In a fully inflated state, the expandable balloon 106 typically has a maximum diameter of about 0.60 inch to about 0.80 inch (e.g., about 0.66 inch to about 0.68 inch).

Still referring to FIG. 2, the light source 110 can be secured to the distal tip 108 of the shaft 102 via crimping or chemical bonding and is typically provided as a light-emitting diode (LED). The light source 110, together with the distal tip 108, forms an atraumatic surface that allows the uterine manipulator 100 to be inserted in the patient without damaging tissues of the vaginal canal, cervix, or uterus. The light source 110 can be turned on and off by actuating a button 119 (e.g., a push button or a slidable button) that is disposed along the manipulator handle 112 and that is electrically coupled to the power source disposed within the manipulator handle 112. The button may generally be disposed along a distal region of the manipulator handle 112 and may be optimally positioned for a right-handed or left-handed user (e.g., a surgeon) of the uterine manipulator 100. Button actuation of the integral light source 110 can provide the user of the uterine manipulator 100 with a simple, ergonomic, and one-handed mechanism for increasing visibility during insertion of the uterine manipulator. The light source 110 can receive power via the one or more electrical wires that extend within the central lumen 120 between the power source and the light source 110. The light source 110 typically operates (e.g., emits light) at a power dissipation of about 100 mW to about 140 mW (e.g., about 108 mW to about 132 mW).

Referring now to FIGS. 1 and 2, the manipulator handle 112 is formed as a clam shell structure that includes a female portion 126 and a male portion 128. The female and male portions 126, 128, respectively, include multiple receptacles 130 (e.g., hexagonal shaped receptacles) and multiple pins (e.g., round or cylindrical shaped pins) positioned along peripheral edges and aligned to mate with each other to hold the female and male portions 126, 128 together. The manipulator handle 112 includes finger depressions 132, 134, 136 that provide a grip to allow the user of the uterine manipulator 100 to ergonomically grip the manipulator handle 112. The manipulator handle 112 further includes an integral syringe 138 for injecting air into and removing air from the central lumen 120 of the shaft 102 to inflate and deflate the expandable balloon 106 in fluid communication with the central lumen 120. A body 140 of the syringe 138 extends distally from the manipulator handle 112 and surrounds an end of the proximal portion 114 of the shaft 102, such that the shaft 102, surrounded by the shrink tube 118 along its proximal portion 114, terminates within the body 140 of the syringe 138. The syringe 138 further includes a plunger 142 that can be actuated (e.g., slid proximally and distally) via a slidable button 144 to inject air into and remove air from the central lumen 120 of the shaft 102. The syringe 138 further includes one or more internal detents in contact with a bottom surface of the button 144 that serve to secure the button 144 in a proximal or distal position upon the button 144 being slid past the detents. Button actuation of the integral syringe 138 can provide the user of the uterine manipulator 100 with a simple, ergonomic, and one-handed mechanism for inflating and deflating the expandable balloon 106 during a surgical procedure.

The shaft 102, the expandable balloon 106, the manipulator handle 112, and the shrink tube 118 of the uterine manipulator 100 can be formed (e.g., molded and/or machined) from one or more materials that are biocompatible and capable of withstanding medical device sterilization procedures, such as chemical-based methods or heat-based methods. In some embodiments, the shaft 102 (e.g., including the proximal portion 114, the central portion 116, and the distal tip 108) can be made of 304 SS and/or 304 SS full hard. Such materials can advantageously provide tactile feedback (e.g., resistance to movement of tissue) to the user of the uterine manipulator 100 as the shaft 102 is inserted or positioned within the patient. In some embodiments, the expandable balloon 106 can be made of silicone, polyvinyl chloride (PVC) or a thermal plastics rubber elastomer (TPRE). In some embodiments, the manipulator handle 112 can be made of polycarbonate or Acrylonitrile butadiene styrene (ABS). In some embodiments, the shrink tube 118 can be made of acrylated olefin and can have a shore durometer of about shore D25 to about shore D60. Such a hardness can provide the shrink tube 118 with enough traction to lock the colpotomizer assembly 104 in a desired location, as will be discussed in more detail with respect to FIGS. 3 and 4. While certain examples of materials from which the shaft 102, the expandable balloon 106, the manipulator handle 112, and the shrink tube 118 can be formed have been provided, it should be understood that a variety of other materials can alternately be used to form these components.

Figure 3:
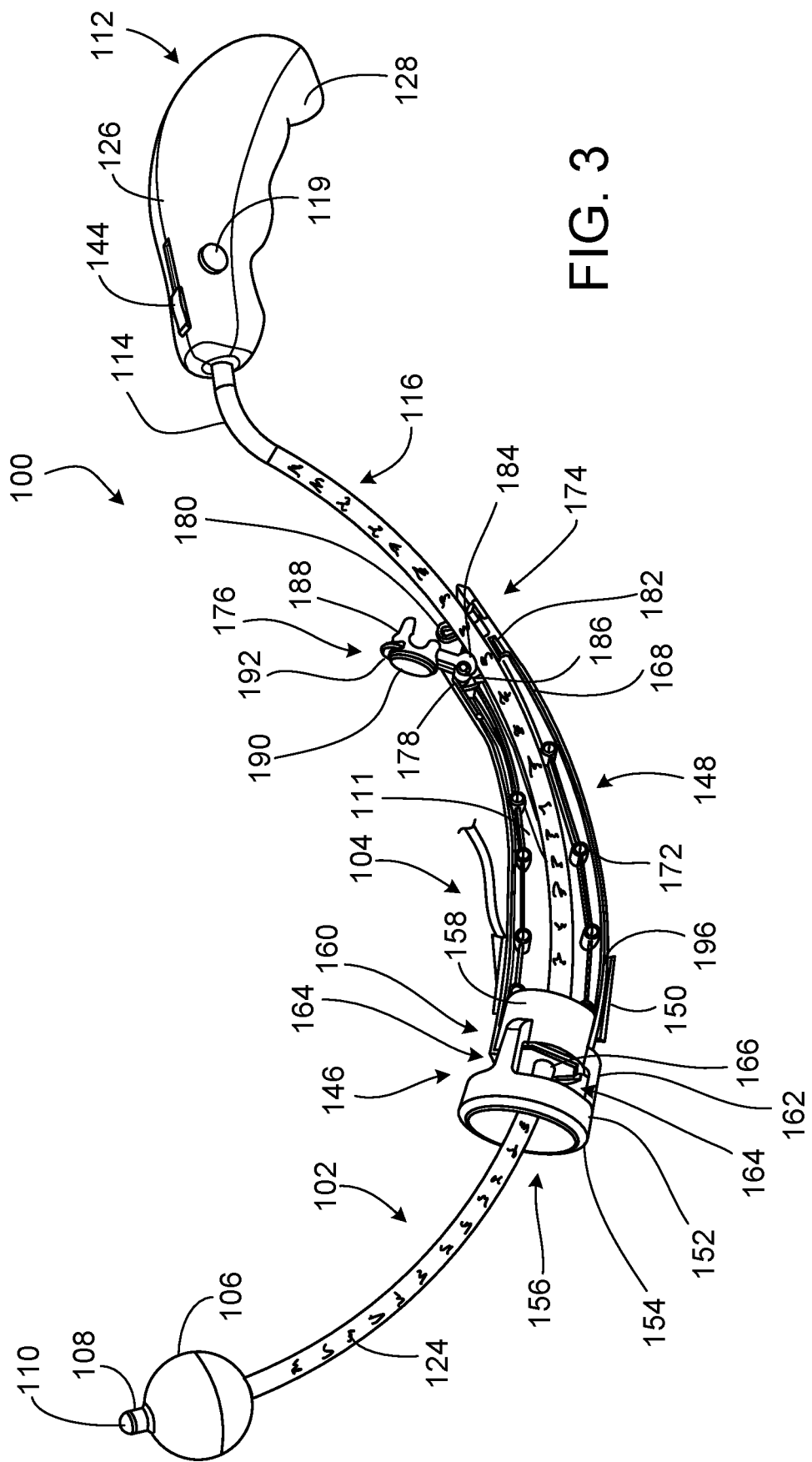
FIG. 3 is a perspective view of a portion of the uterine manipulator of FIG. 1, shown with portions of the colpotomizer assembly removed and with the colpotomizer assembly in an unlocked configuration.

Referring to FIGS. 1 and 3, the colpotomizer assembly 104 is a displaceable assembly that may be slid along the shaft 102 of the uterine manipulator 100. The ability to displace the colpotomizer assembly 104 can allow for quicker and easier positioning of the distal tip 108 of the shaft 102 within the cervix since this procedure can be performed without the visual obstruction of the colpotomizer assembly 104. Then, once proper placement of the distal tip 108 is visually confirmed, the colpotomizer assembly 104 can be advanced along the shaft 102 into engagement with the cervix. The colpotomizer assembly 104 includes a colpotomizer cup 146 adapted to receive the cervix, a sleeve 148 that is connected to the colpotomizer cup 146 and that can be grasped for moving the colpotomizer assembly 104, and a vaginal occluder 150 disposed about a distal cuff 196 of the sleeve 148.

Referring to FIGS. 3-7, the colpotomizer cup 146 includes an annular body 152, a rim 154 located at a distal end 156 of the body 152, and a base 158 located at a proximal end 160 of the body 152. The rim 154 is beveled to permit anatomical landmark and incision backstop during use of the uterine manipulator 100. The body 152 includes three projections 162 that extend to the base 158 and define three viewing windows 164. The base 158 of the colpotomizer cup 146 defines an opening 166 sized to allow passage of the shaft 102. A wall of the opening 166 defines a cylindrical profile through which the shaft 102 passes (refer to FIG. 11).

The colpotomizer cup 146 typically has a maximum inner diameter (e.g., along an internal surface of the body 152, at an edge of the rim 154) that is in a range of about 2.5 cm to about 4.0 cm. For example, the colpotomizer cup 146 may be selectable from multiple predetermined sizes for use on patients with a range of vaginal and uterine anatomical feature sizes. In some embodiments, the colpotomizer cup 146 has a maximum inner diameter of about 2.5 cm, about 3.0 cm, about 3.5 cm, or about 4.0 cm. In some embodiments, each of the viewing windows 164 extends about 60° to about 120° about a circumference of the body 152 of the colpotomizer cup 146, such that the three viewing windows 164 together extend about a majority of the circumference of the body 152 to optimize visibility of the base of the uterus contained therein during a surgical procedure. The viewing windows 164 typically have a height that is in a range of about 1.0 cm to about 1.2 cm.

In certain embodiments, the body 152 of the colpotomizer cup 146 has a wall thickness that ranges from about 0.2 cm to about 0.7 cm. In some embodiments, the body 152 has a minimum wall thickness along a platform 123 of the base 158 of the colpotomizer cup 146. In some embodiments, the body 152 has a maximum wall thickness at proximal ends 125 of the projections 162.

Figure 8:
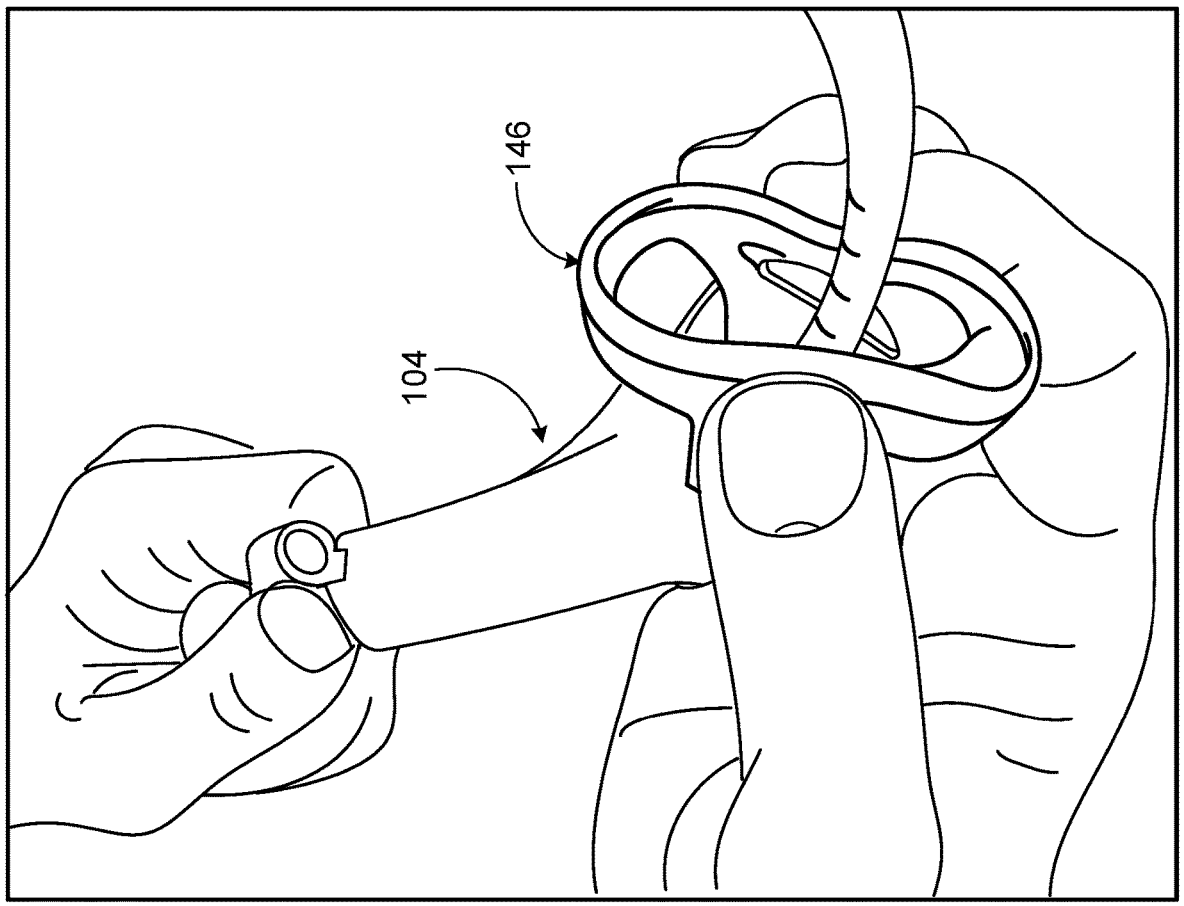
FIG. 8 is an illustration of a user squeezing the colpotomizer cup of FIG. 5 into a reduced size configuration.
Figure 7:
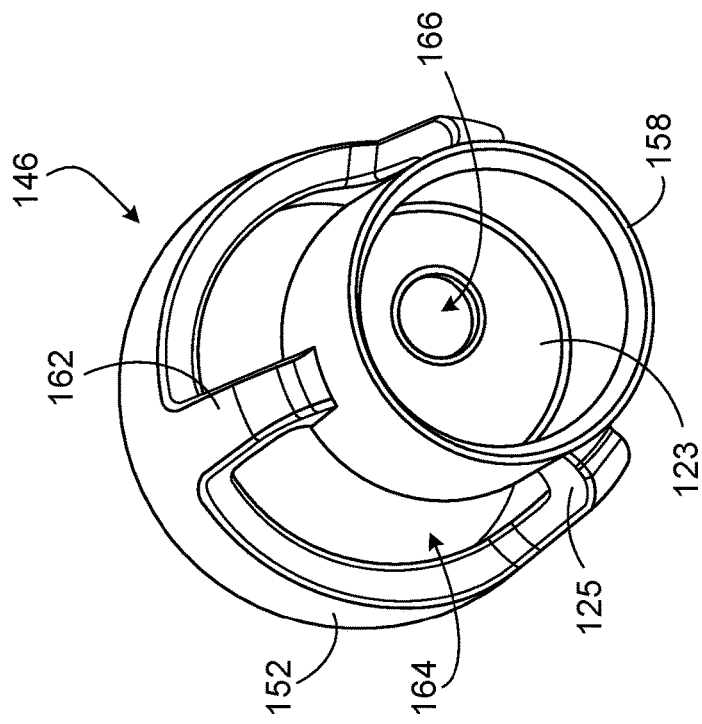
FIG. 7 is a bottom perspective view of the colpotomizer cup of FIG. 5.

In some embodiments, the colpotomizer cup 146 is formed of one or more materials that can reversibly deform. For example, such materials can rebound from a reduced size configuration (e.g., in which the material has been bent due to application of an external compression force) to a nominal size configuration (e.g., a resting configuration absent an external compression force). Such materials, together with a geometry of the colpotomizer cup 146 (e.g., including the wall thickness of the body 152 and void spaces formed by the viewing windows 164), can allow flexible adjustment of the colpotomizer cup 146 for insertion of the uterine manipulator 100 into a patient. Accordingly, as shown in FIG. 8, the colpotomizer cup 146 can be squeezed into a collapsed configuration (e.g., such that the colpotomizer cup 146 is folded upon itself) to facilitate insertion of the colpotomizer cup 146 into a vaginal entryway (e.g., the vaginal introitus) of a relatively small size (e.g., with a width of about 1.9 cm to about 2.6 cm (mean)). In some examples, such a reduced size configuration (e.g., reduced width configuration) of the colpotomizer cup 146 can prevent the need for a user (e.g., a surgeon) to cut the vaginal wall near the vaginal entryway to enlarge the vaginal entryway for allowing insertion of an otherwise larger sized colpotomizer cup.

The collapsed configuration of the colpotomizer cup 146 can also facilitate placement of the colpotomizer cup 146 within the vaginal vault. Although the vaginal vault is larger (e.g., wider) than the vaginal canal, placing a colpotomizer cup within the vaginal vault can be difficult to do in cases where the vaginal vault has thinned tissue that can be easily torn or lacerated. An atrophic vaginal state that can result in a small vaginal entryway or a mechanically compromised vaginal vault is often found in elderly patients, in patients who have been diagnosed with certain diseases (e.g., cancer, fibroids, endometriosis, abnormal uterine bleeding and adhesions), or in patients who have previously undergone certain surgeries or treatments (e.g., total laparoscopic hysterectomy (TLH), laparoscopic supracervical hysterectomy (LSH), and laparoscopically assisted vaginal ysterectomy (LAVH)).

Example deformable materials from which the colpotomizer cup 146 is typically made includes polyether based materials, such as thermoplastic polyurethane, or other deformable materials, such as silicone, santoprene, and polypropylene. Such deformable materials have one or more properties that allow the colpotomizer cup 146 to maintain its mechanical integrity upon application of typical forces that would be applied to the colpotomizer cup 146 during a surgical procedure. For example, such materials typically have an elastic modulus in a range of about 5.5 MPa to about 171 MPa, a hardness in a range of 85 Shore A to 100 Shore A, a tensile strength in a range of about 15.5 MPa to about 62 MPa, and a tear strength of about 78.9 N/mm to about 701 N/mm. In some embodiments, the colpotomizer cup 146 is manufactured via one or more techniques including extrusion and injection molding.

Referring again to FIG. 3, the sleeve 148 extends proximally from the base 158 of the colpotomizer cup 146 and has an arcuate shape that generally follows the shape of the central portion 116 of the shaft 102. The sleeve 148 is formed as a clam shell structure that includes a female portion 168 and a male portion 170 (shown in FIG. 1). The female and male portions 168, 170, respectively, include multiple receptacles 172 (e.g., hexagonal shaped receptacles) and multiple pins (e.g., round or cylindrical shaped pins) positioned along peripheral edges and aligned to mate with each other to secure the female and male portions 168, 170 together. The female and male portions 168, 170 together define a channel 111 through which the shaft 102 extends.

At a proximal end 174 of the sleeve 148, the sleeve 148 includes a thumb lock 176, opposing receptacles 178 that receive the thumb lock 176, opposing projections 180 to which the thumb lock 176 can be snap fitted, and a guide surface 182 that appropriately guides the sleeve 148 along the shaft 102 and supports the shaft 102 for contact with the thumb lock 176. The thumb lock 176, receptacles 178, projections 180, and guide surface 182 together provide a quick, one-handed locking mechanism that allows the colpotomizer assembly 104 to be locked into a desired position along the shaft 102.

Figure 4:
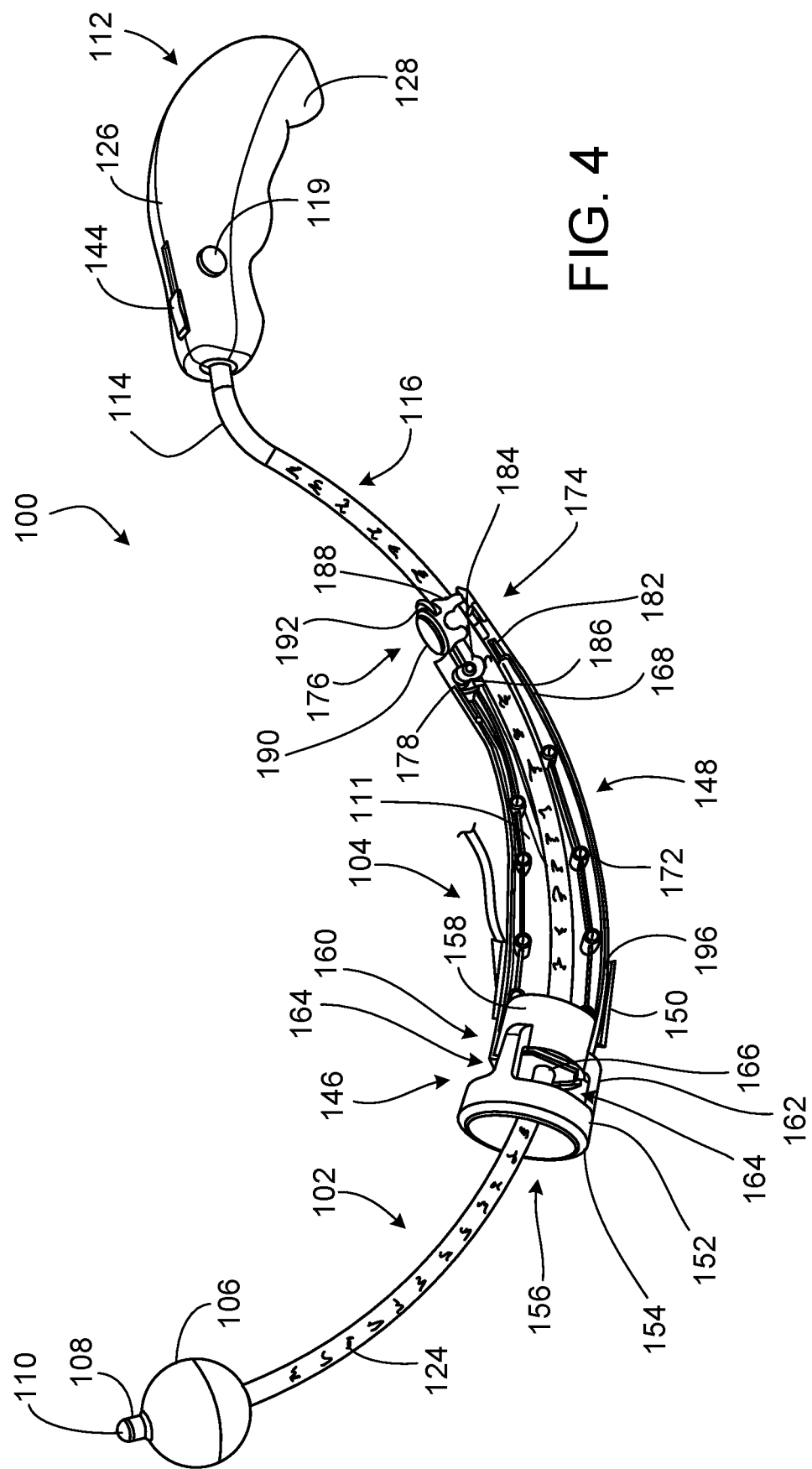
FIG. 4 is a perspective view of a portion of the uterine manipulator of FIG. 1, shown with portions of the colpotomizer assembly removed and with the colpotomizer assembly in a locked configuration.
Figure 5:
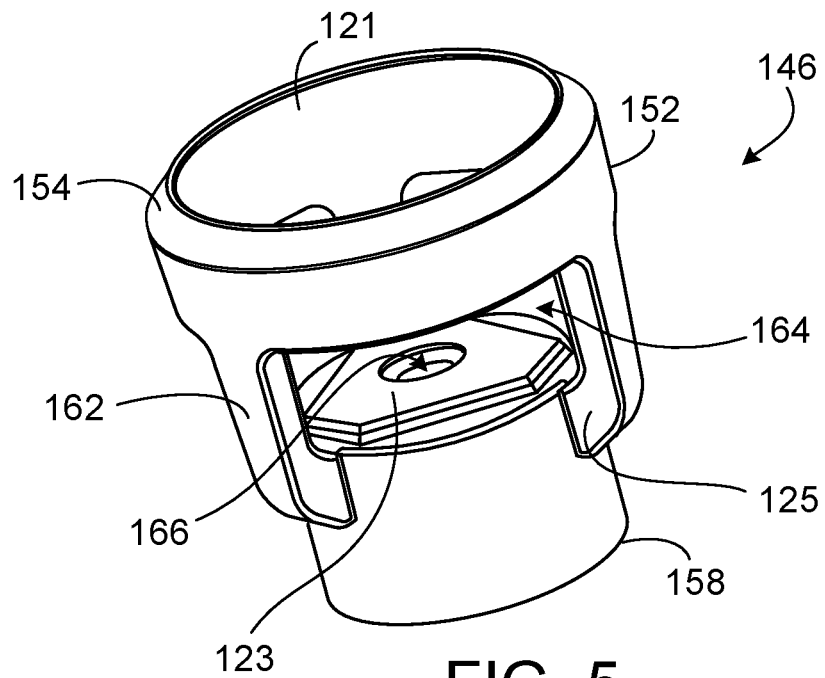
FIG. 5 is a perspective view of a colpotomizer cup of the colpotomizer assembly of FIG. 1 in a nominal size configuration.
Figure 6:
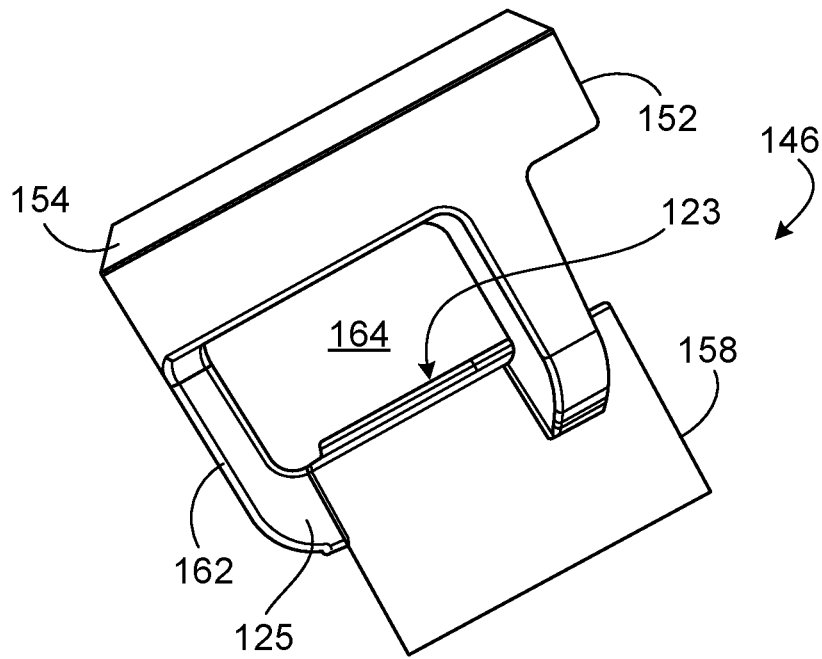
FIG. 6 is a side view of the colpotomizer cup of FIG. 5.

Referring to FIGS. 3 and 4, the thumb lock 176 includes a cam roller 184 adapted to contact the shrink tube 118 surrounding the shaft 102 to lock the colpotomizer assembly 104 into a selected position along the shaft 102. In particular, the radius of the cam roller 184 is variable (e.g., extending radially beyond a minimum circumference of the cam roller 184 along certain portions of the cam roller 184), such that the cam roller 184 compresses (e.g., digs into) the shrink tube 188 as the cam roller 184 is rotated towards the shaft 102 of the uterine manipulator 100. The thumb lock 176 further includes a roller mount 186 adjacent the cam roller 184, a jaw 188 extending from the cam roller 184, a lens 190 disposed atop the jaw 188, and a lift flange 192 extending proximally from the jaw 188. The lens 190 is a convex lens that magnifies the ruler markings 124 printed along the shaft 102. The focal point of the lens 190 is selected such that a ruler marking 124 substantially fills the viewing window of the lens 190. Such magnification assists the user of the uterine manipulator 100 in visualizing the ruler markings 124 to determine the position of the colpotomizer assembly 104 along the shaft 102. The roller mount 186 is adapted to extend into and rotate within the receptacles 178.

The thumb lock 176 allows the colpotomizer assembly 104 to be locked into a desired position using an easy, one-handed technique that can be carried out with the same hand that moves the colpotomizer assembly 104 along the shaft 102. When the lens 190 or the lift flange 192 is pushed downward (e.g., by the user's thumb) towards the shaft 102 to place the thumb lock 176 in a closed configuration (shown in FIG. 4), rotation of the roller mount 186 and associated rotation of the cam roller 184 causes the cam roller 184 to dig into the shrink tube 118, thereby generating friction that locks the sleeve 148 of the colpotomizer assembly 104 in position along the shaft 102. The cam roller 184 of the thumb lock 176 is configured to apply a compressive load of up to about 5 lb to about 10 lb (e.g., about 7 lb to about 8 lb) on the shaft 102. Such downward force applied to the lens 190 or to the lift flange 192 also causes the jaw 188 to snap fit onto the projections 180. When the lift flange 192 is pushed upward (e.g., by the user's thumb) away from the shaft 102 to place the thumb lock 176 in an open configuration (shown in FIG. 3), rotation of the roller mount 186 and associated rotation of the cam roller 184 causes the cam roller 184 to release the shrink tube 118, thereby unlocking the sleeve 148 of the colpotomizer assembly 104 with respect to the shaft 102. Such upward force applied to the lift flange 192 also causes the jaw 188 to separate from the projections 180. The thumb lock 176 provides the user with the ability to lock the colpotomizer assembly 104 at various different positions along the shaft 102 of the uterine manipulator 100.

Figure 9:
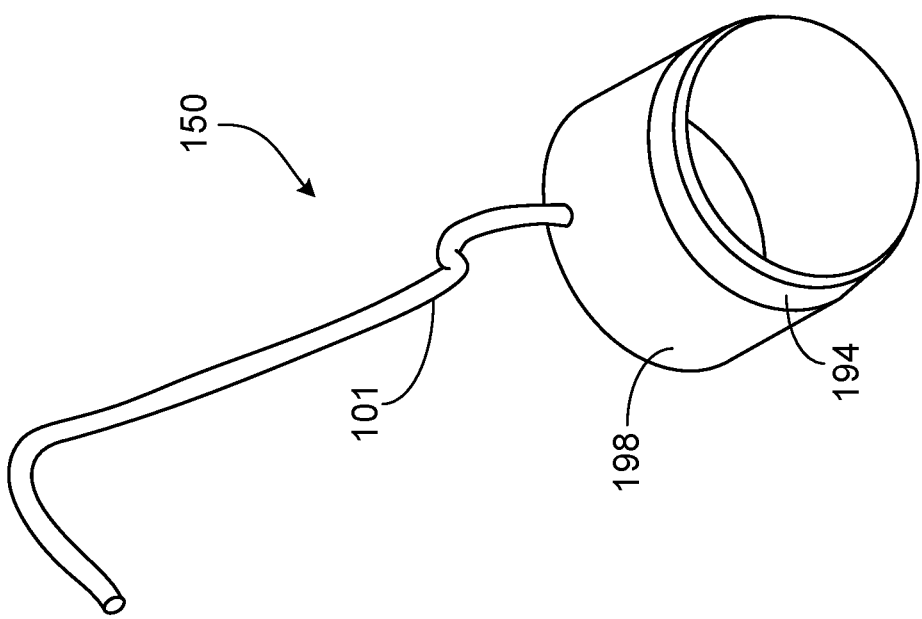
FIG. 9 is a perspective view of a vaginal occluder of the colpotomizer assembly of FIG. 1.

As shown in FIG. 9, the vaginal occluder 150 includes a main body 194 that can be mounted concentrically about the distal cuff 196 of the sleeve 148, an expandable balloon cuff 198, and a balloon cuff catheter tube 101. The balloon cuff catheter tube 101 is affixed to the balloon cuff 198 and communicates fluid to the balloon cuff 198 when inflation is desired.

Figure 10:
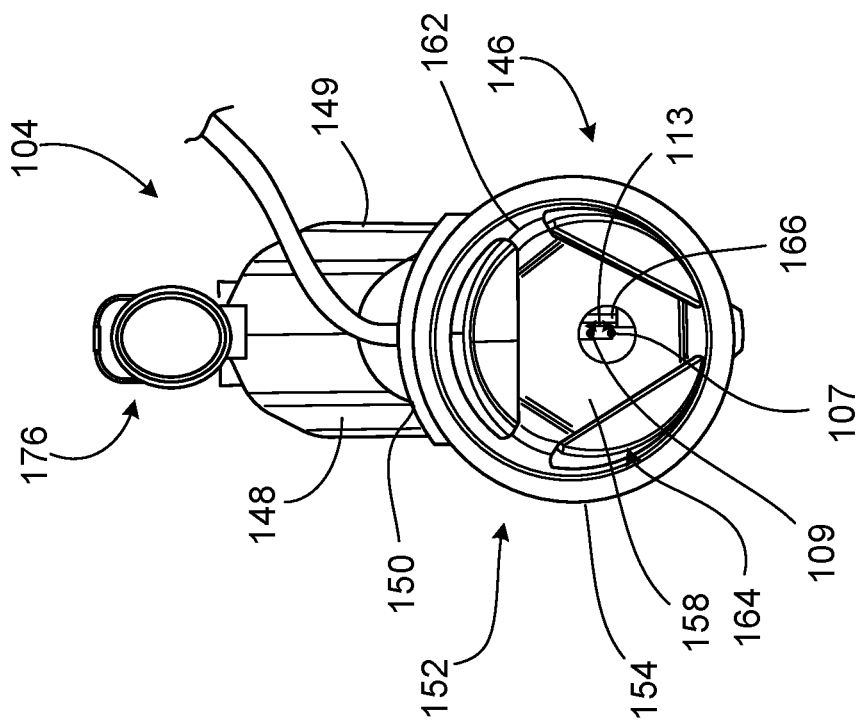
FIG. 10 is a front perspective view of the colpotomizer assembly of FIG. 1.
Figure 11:
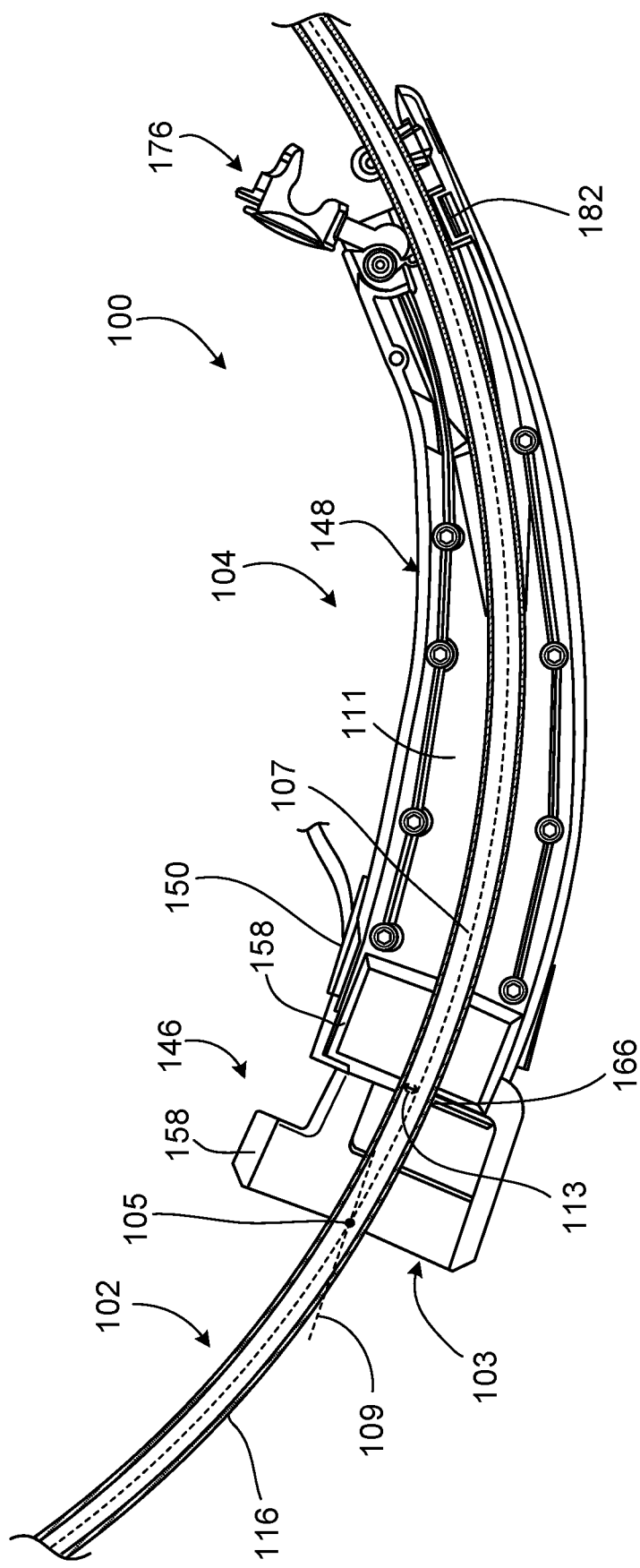
FIG. 11 is a cross-sectional side view of a portion of the uterine manipulator of FIG. 1.

Referring to FIGS. 10 and 11, the colpotomizer assembly 104 of the uterine manipulator 100 has a geometry (e.g., provided by the position and size of the opening 166 of the base 158) that ensures proper alignment of the cup face 103 with respect to the shaft 102. The cup face 103 is oriented perpendicular (e.g., normal) to an axial centerline 109 of the colpotomizer cup 146. A centerpoint 105 of the cup face 103 (located along the axial centerline 109 of the colpotomizer cup 146) is maintained along an arch centerline 107 of the shaft 102 as the colpotomizer assembly 104 is slid along the shaft 102. Such alignment of the cup face 103 with the arch centerline 107 is provided by an offset 113 between the centerline 109 of the colpotomizer cup 146 and the arch centerline 107 of the shaft 102, at the location of the opening 166 of the base 158 of the colpotomizer cup 146. The offset 113 is typically a distance of about 0.065 inch to about 0.085 inch (e.g., about 0.071 inch to about 0.081 inch). The colpotomizer cup 146 is substantially prevented from tilting with respect to the shaft 102 by points of contact between the cup 146 and the shaft 102 at the opening 166 of the base 158 and the roller mount 182 and cam lock 184 of the thumb lock 176. Aligning the colpotomizer cup 146 with respect to the shaft 102 in this manner ensures that an appropriately angled cutting edge is achieved for guiding a cutting of the uterus with an even distribution of tissue when the cervix is received within the colpotomizer cup 146. In other words, this configuration can help to ensure that substantially the same amount of cervical tissue is received in the colpotomizer cup 146 about the entire circumference of the shaft 102, and can thus help to ensure that a symmetrical cut is made to the cervix during a surgical procedure, such as a hysterectomy.

The various components of the colpotomizer assembly 104 can be formed (e.g., molded and/or machined) from one or more materials that are biocompatible. For example, as discussed above, the colpotomizer cup 146 can be made of a thermoplastic polyurethane. In some embodiments, the female and male portions 168, 170 of the sleeve 148 can be made of acrylonitrile butadiene styrene (ABS). In some embodiments, certain components of the thumb lock 176 (e.g., the cam roller 184, the roller mount 186, the jaw 188, and the lift flange 192) can be made of polycarbonate. In some embodiments, the various components of the vaginal occluder 150 can be made of medical grade silicone. In some embodiments, the colpotomizer cup 146 and the sleeve 148 are formed (e.g., molded) as separate items that can then be connected together (e.g., via press fit or snap fit). This two-piece assembly can allow cup bodies of different sizes (e.g., different diameters) to be used with the same sleeve. While certain examples of materials with which the components of the colpotomizer assembly 104 can be formed have been described, it should be understood that other materials can alternately be used to form these components.

Figure 12:
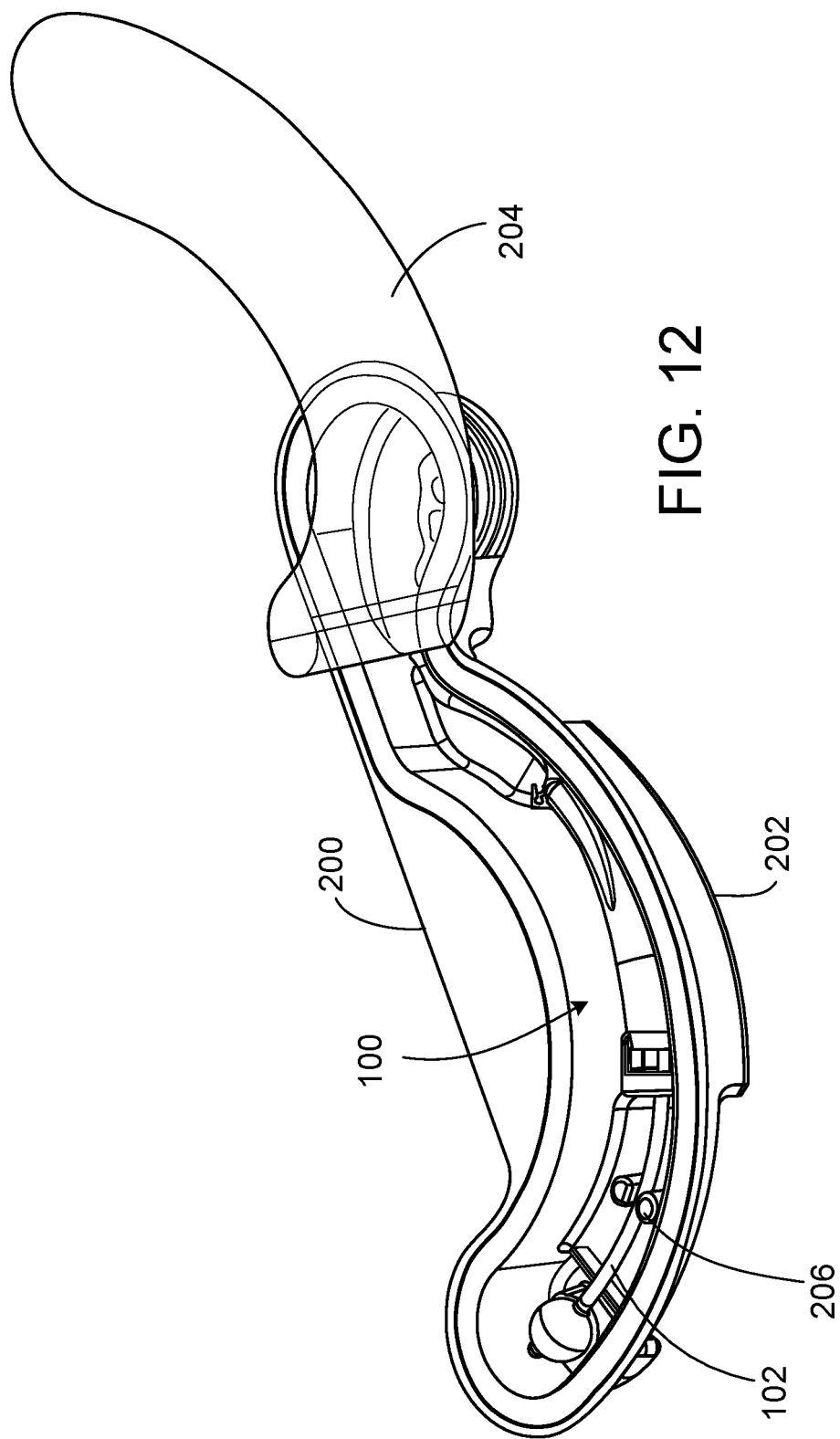
FIG. 12 is a perspective view of the uterine manipulator of FIG. 1 provided in a packaging container.

Referring to FIG. 12, in some embodiments, the uterine manipulator 100 is provided as a disposable (e.g., single-use) surgical device that is housed in a packaging container 200. The packaging container 200 provides an easy-to-open structure that allows for secure, space-saving transport and storage of the uterine manipulator 100. The packaging container 200 includes a base 202 that houses the uterine manipulator 100 and a cover 204 that can be peeled from the base 202 to open the packaging container 200. The base 202 of the packaging container 200 has a shape that generally follows the shape of the uterine manipulator 100. The base 202 of the packaging container 200 includes spaced apart posts 206 that secure the shaft 102 of uterine manipulator 100 in a stable position. The packaging container 200 can be transparent, translucent, or opaque and can be made of one or more materials that are biocompatible. For example, the packaging container 200 can be made of Ethylene-vinyl acetate.

The uterine manipulator 100 may be used in a number of procedures that require manipulation of the uterus, including surgical procedures, such as hysterectomies. In one example, the uterine manipulator 100 is used in a total laparoscopic hysterectomy (TLH) surgery. A patient is prepared for TLH surgery according to know procedures. Such procedures can include determining a depth of the uterus (e.g., as measured from the fundus of the uterus to the cervical os) using a sounding device or an ultrasound technique. For example, a sounding device that has ruler markings along its length may be inserted into the patient until a distal end is positioned adjacent the fundus of uterus according to visual confirmation of the depth reading at the cervix. The ruler marking located at the depth of the uterus (i.e., at the proximal end of the cervix) indicates the location where the colpotomizer cup 146 of the colpotomizer assembly 104 should be placed during the surgical procedure. In other words, the depth of the uterus corresponds to an operational position of the colpotomizer cup 146 for carrying out the procedure. As discussed above with respect to FIGS. 2-4, the ruler markings 124 along the shaft 102 of the uterine manipulator 100 indicate a distance from the fundus to the base 158 of the colpotomizer cup 146 when the uterine manipulator 100 is appropriately, fully inserted within the patient. The ruler markings 124 along the shaft 102 compensate for an arc length of the colpotomizer assembly 104, thereby reflecting an accurate depth placement of the colpotomizer cup 146. Proper placement of the uterine manipulator 100 with respect to the fundus, as aided by the lens 190 of the thumb lock 176 and the ruler markings 124 along the shaft 102, can prevent perforation and other damage to the fundus and the distal region of the uterus.

Figure 13:
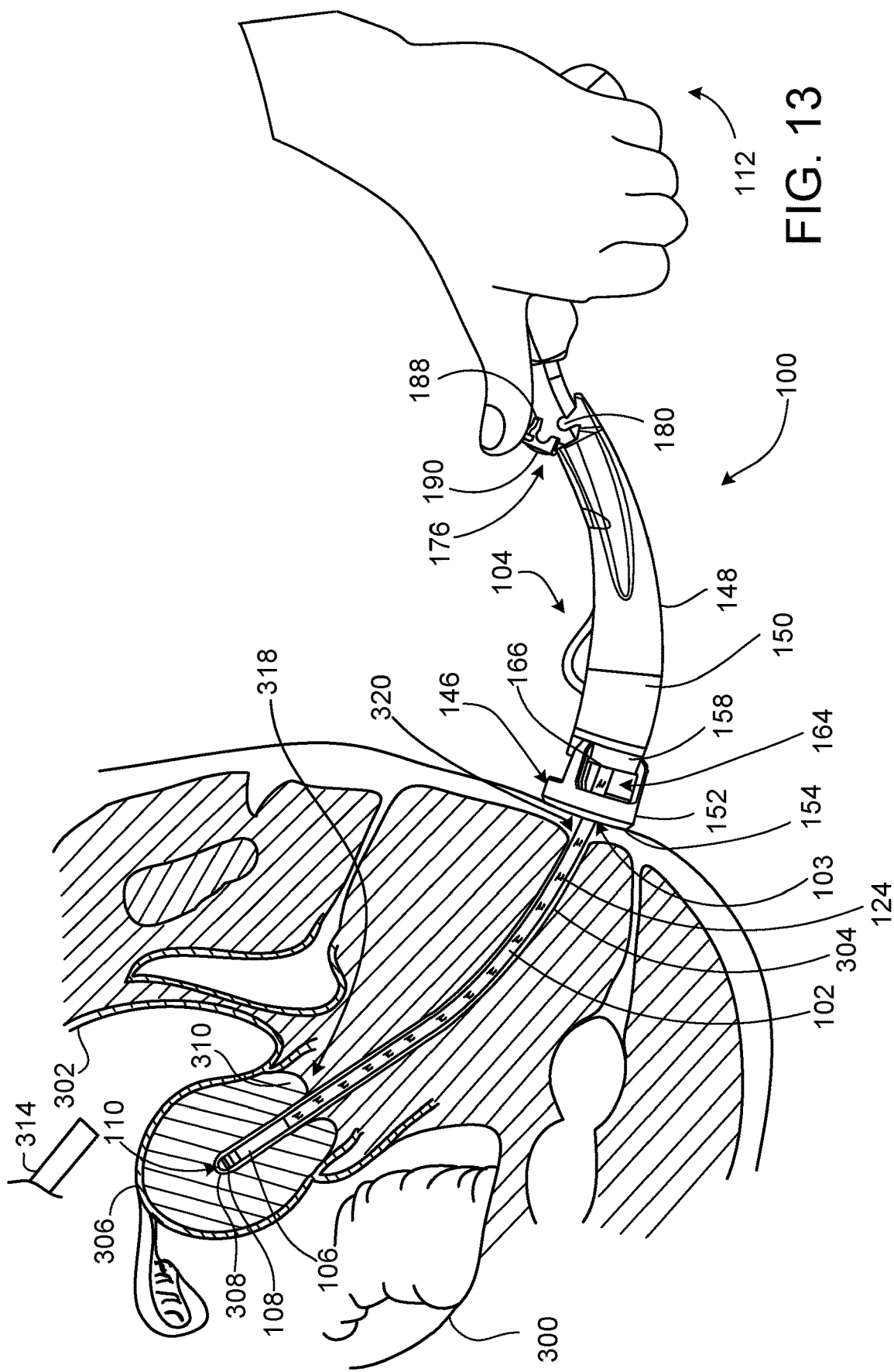
FIG. 13 is a cross-sectional side view of a pelvic cavity of a patient showing the uterine manipulator of FIG. 1 in a fully inserted position and with the colpotomizer assembly in a loading position.

FIGS. 13-17 illustrate a method of using the uterine manipulator 100. Referring particularly to FIG. 13, once prepared, the patient's peritoneal cavity 300 is inflated with a gas (e.g., $CO_2$) to facilitate accessibility and visibility of the female pelvic organs and surgical instruments (e.g., a laparoscope 314) as the instruments are inserted through the abdominal wall 302 and into the peritoneal cavity 300. The colpotomizer assembly 104, while in an unlocked configuration, is slid proximally along the shaft 102 until the colpotomizer assembly 104 reaches a loading position (e.g., a position where the proximal end 174 of the sleeve 148 is positioned along the proximal portion 114 of the shaft 102). The button 119 located along the manipulator handle 112 for controlling the light source 110 is actuated (e.g., depressed or slid) to turn on the light source 110. Next, the uterine manipulator 100, with the colpotomizer assembly 104 in the loading position and with the light source 110 turned on, is inserted into the vaginal canal 304. Light emitted from the light source 110 improves visibility of the vaginal canal 304 as the uterine manipulator 100 is inserted. In some cases, the colpotomizer assembly 104 is locked in the loading position prior to insertion into the vaginal canal 304. In other instances, the colpotomizer assembly 104 remains unlocked in the loading position during insertion into the vaginal canal 304.

Figure 14:
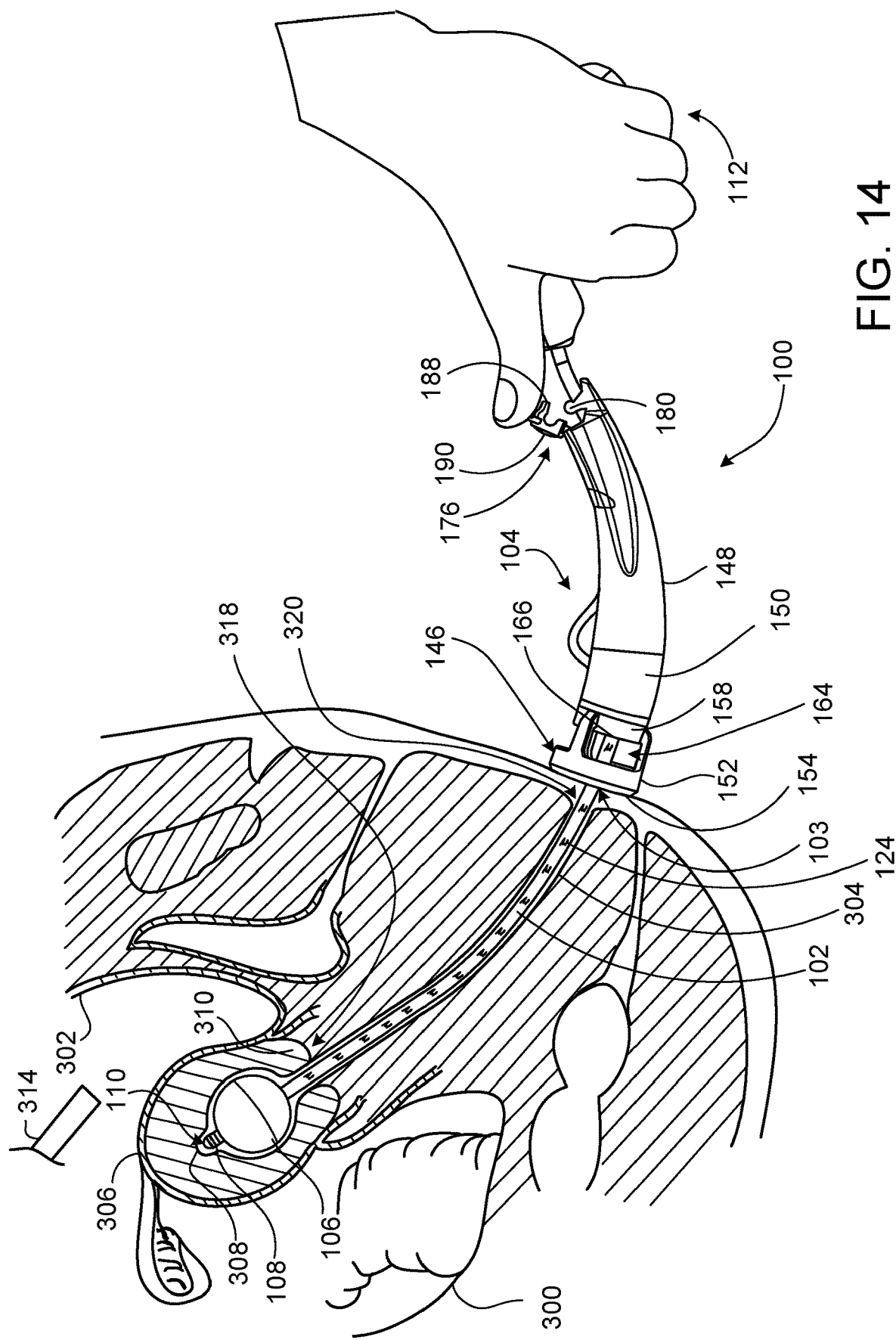
FIG. 14 is a cross-sectional side view of the pelvic cavity of FIG. 13, showing the uterine manipulator of FIG. 1 in a fully inserted position, with the expandable balloon inflated, and with the colpotomizer assembly unlocked in the loading position.

Referring to FIG. 14, the uterine manipulator 100 is moved distally within the vaginal canal 304 until the distal tip 108 of the shaft 102 is positioned adjacent the fundus 308 of the uterus. The slidable button 144 of the syringe 138 is then slid distally (as shown in FIG. 2) to inflate the expandable balloon 106 such that the expandable balloon 106 engages an interior surface of the uterus 306. In some cases, the slidable button 144 may be slid proximally to deflate the expandable balloon 106 if it is determined that the uterine manipulator 100 needs to be repositioned. Leaving the colpotomizer assembly 104 in the loading position during insertion of the uterine manipulator 100 can allow for a relatively unobstructed view of the cervix 310 to help ensure proper placement of the distal tip 108 of the shaft 102.

Figure 15:
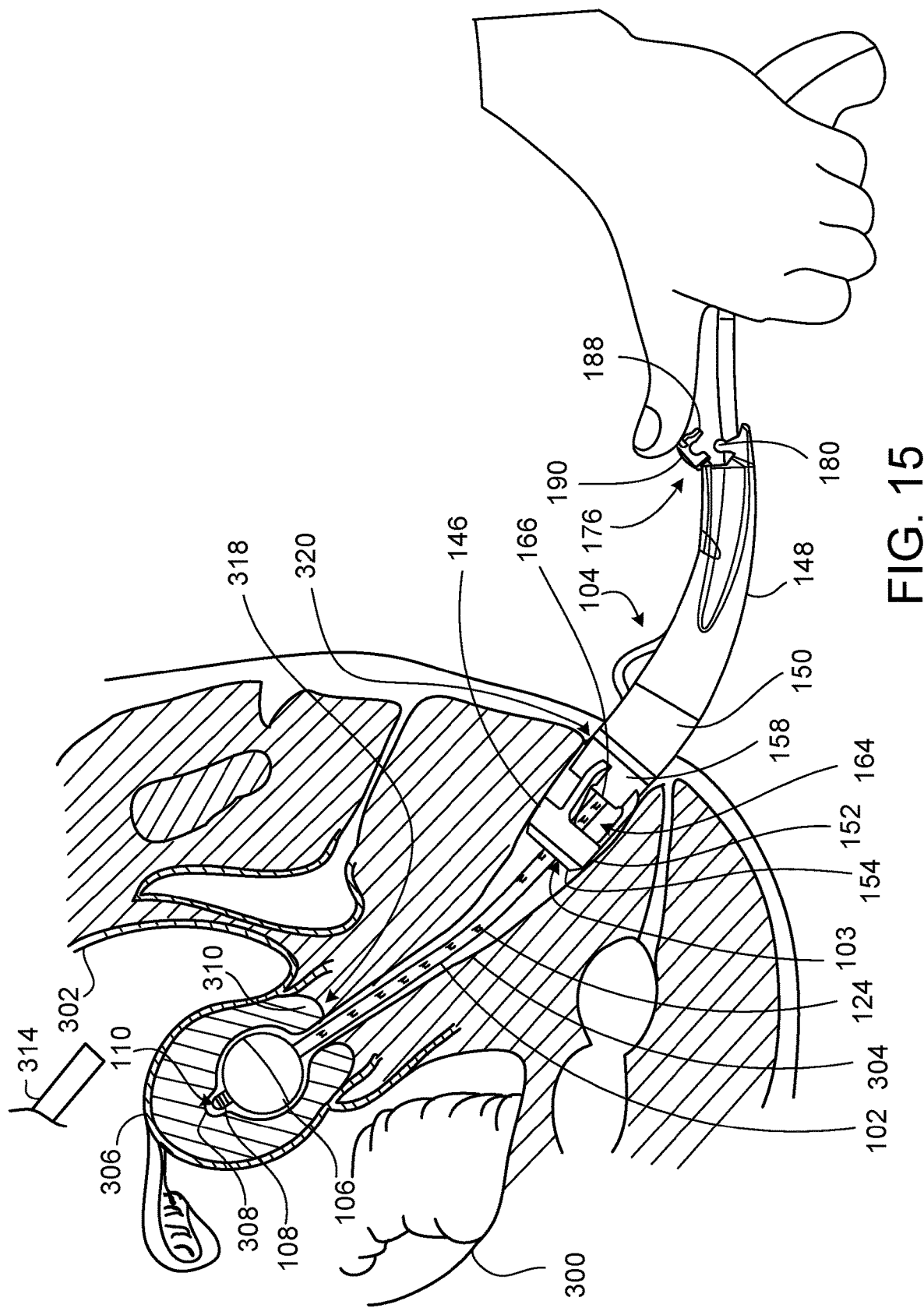
FIG. 15 is a cross-sectional side view of the pelvic cavity of FIG. 13, showing the uterine manipulator of FIG. 1 fully inserted, with the colpotomizer cup in a reduced size configuration within an entryway of the vagina of the patient.
Figure 16:
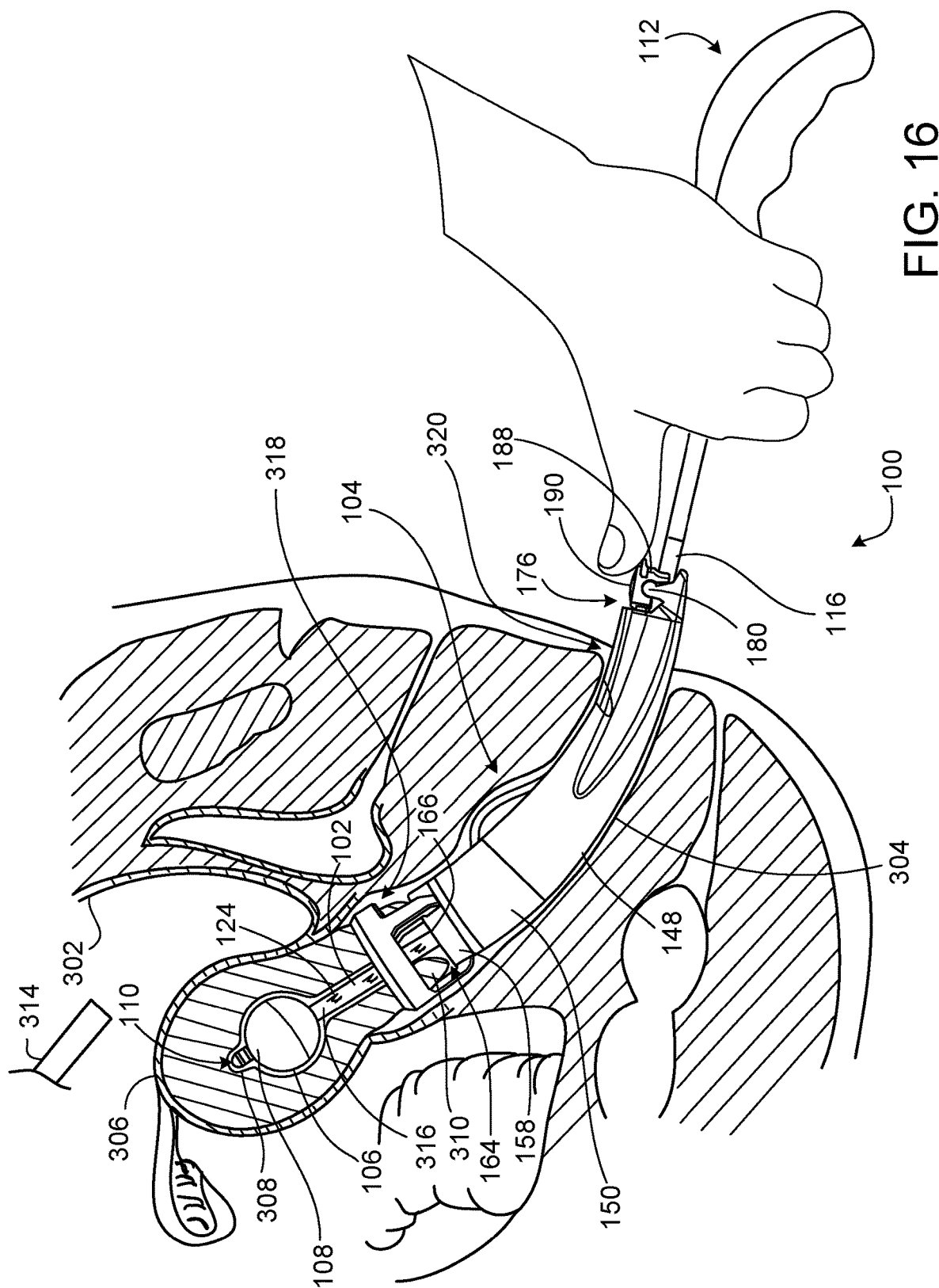
FIG. 16 is a cross-sectional side view of the pelvic cavity of FIG. 13, showing the uterine manipulator of FIG. 1 fully inserted, with the colpotomizer assembly locked in an operational position and with the colpotomizer cup in a nominal size configuration and surrounding the cervix of the patient.

Referring to FIG. 15, the colpotomizer cup 146 of the colpotomizer assembly 104 is squeezed into a reduced size configuration (e.g., a collapsed, reduced width configuration) and inserted into the vaginal entryway 320 of the vaginal canal 304. Referring to FIG. 16, the colpotomizer assembly 104 (still in the unlocked configuration and still maintained in the reduced size configuration by the wall of the vaginal canal 304) is advanced distally from the loading position until the ruler markings 124 (as visualized through the lens 190) indicate that the base 158 of the colpotomizer cup 146 is positioned at an operational position (i.e., at a distance from the distal tip 108 that is approximately equal to the depth of the uterus 306 as determined from the sounding device, and within a vaginal vault 318 of the patient). The viewing windows 164 of the colpotomizer cup 146 can provide for additional visual confirmation of placement.

In the operational position, the colpotomizer cup 146 expands to its nominal size configuration (e.g., or nearly to its nominal size configuration) within the vaginal vault 318 (e.g., which is larger than the vaginal canal 304) such that the cervix 310 can be positioned within the body 152 of the colpotomizer cup 146 and abut the base 158 of the colpotomizer cup 146. The alignment of the lens 190 with the ruler marking 124 and the ability to view placement of the cervix 310 within the colpotomizer cup 146 through the viewing windows 164 helps to ensure that the colpotomizer cup 146 is fully forward in the desired position relative to the distal tip 108 of the shaft 102 and relative to the cervix 310. In this position, the colpotomizer cup 146 provides an anatomical landmark at the base of the uterus 306 (e.g., indicating a location of an apex of the cervix 310) and an incision backstop (e.g., an edge that defines where the uterus 306 should be cut). Furthermore, the cup face 103 of the colpotomizer cup 146 is centered on the arch centerline 107 of the shaft 102, ensuring a proper angular position of the colpotomizer cup 146 with respect to the shaft 102 for providing a desirable or suitable cutting guide.

With the colpotomizer assembly 104 positioned as desired, the jaw 188 of the thumb lock 176 is then depressed to lock the colpotomizer assembly 104 at the operational position. The jaw 188 can be depressed using the same hand that advances the colpotomizer assembly 104 within the vaginal canal 304, such that distal movement and locking of the colpotomizer assembly 104 can be performed in a one-handed operation. If necessary, the lift flange 192 of the thumb lock 176 can be pushed upwards to unlock the colpotomizer assembly 104 for repositioning along the shaft 102. In some implementations, the mechanical integrity of the thumb lock 176 may be maintained over multiple (e.g., four) lock-unlock cycles.

Figure 17:
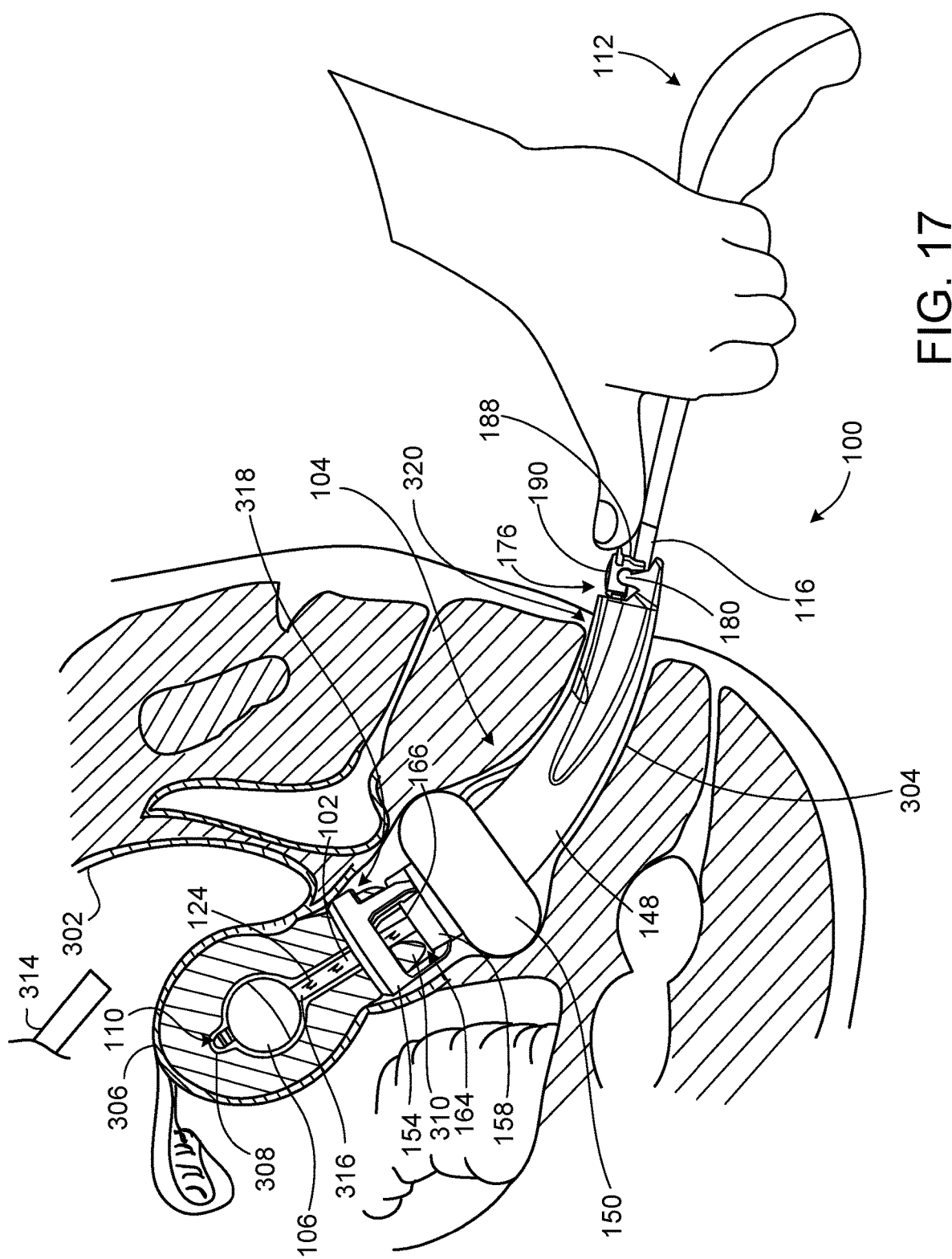
FIG. 17 is a cross-sectional side view of the pelvic cavity of FIG. 13, showing the uterine manipulator of FIG. 1 supporting the uterus of the patient.

Referring to FIG. 17, once the colpotomizer assembly 104 is locked in the desired operational position along the shaft 102, the vaginal occluder 150 can be inflated (e.g., with a sterile, water-based fluid) to seal a distal region of the vaginal canal 304, thereby maintaining pneumoperitoneum. The vaginal occluder 150 inhibits (e.g., prevents) the escape of gas used to inflate the peritoneal cavity 300 during and following the first of any colpotomy incisions.

A surgeon can then manipulate or move the uterus 306 into a desired position to perform surgical procedures that include cutting around the base of the uterus 306. As discussed above, the offset 113 (located at the opening 166 in the base 158 of the colpotomizer cup 146) between the centerline 109 of the colpotomizer cup 146 and the arch centerline 107 of the shaft 102 ensures that the centerpoint 105 of the cup face 103 is located along the arch centerline 107 of the shaft 102. Such a configuration prevents undesired tilting of the colpotomizer cup 146 relative to the shaft 102, such that cutting along the cup face 103 results in a symmetrical cut of the uterus 306 with an even distribution of tissue within the colpotomizer cup 146. After the uterus 306 is completely incised such that the uterus 306 is totally free in the peritoneal cavity 300 and held only by the uterine manipulator 100, then the uterine manipulator 100, along with the supported uterus 306, is removed through the vaginal canal 304. The uterine manipulator 100 can be disposed of following the surgery.

While certain embodiments have been described above, other embodiments are possible.

For example, while the locking mechanism of the colpotomizer assembly 104 is described as being located at the proximal end 174 of the sleeve 148, in other embodiments, a locking mechanism may be located a different location (e.g., at an intermediate location) along a length of a colpotomizer assembly.

While a specific configuration of a one-handed cam-based locking mechanism has been described, other types of locking mechanisms can be used. In certain embodiments, for example, a uterine manipulator may include a different type of one-handed cam-based locking mechanism. Such example locking mechanisms may include a screen door mechanism, a Touhy Borst mechanism, or a sheet metal skive capture mechanism.

While the colpotomizer assembly 104 has been described as including a one-handed locking mechanism, in some embodiments, a uterine manipulator may include a colpotomizer assembly that has a two-handed locking mechanism.

While the uterine manipulator 100 has been described as including the integral syringe 138, in some embodiments, a uterine manipulator may not include an integral syringe. For example, in some embodiments, a syringe may alternatively be secured externally to a proximal end of a manipulator handle of a uterine manipulator.

While the uterine manipulator 100 has been described as including the integrated light source 110, in some embodiments, a uterine manipulator may not include an integrated light source. For example, in some embodiments, a uterine manipulator may be used with a separate or external light source. In other examples, a uterine manipulator may be used without a light source.

While the uterine manipulator 100 has been described as disposable, in some embodiments, the uterine manipulator 100 may be reusable (e.g., sterilizable).

While the uterine manipulator 100 has been described and illustrated as having certain dimensions, shapes, and profiles, in some embodiments, a uterine manipulator that is otherwise similar in construction and function to the uterine manipulator 100 may include one or more components that have one or more dimensions, shapes, or profiles that are different from those described above with respect to the uterine manipulator 100.

What is claimed is:

1. A method of positioning a uterine manipulator within a patient, the method comprising:
   grasping a colpotomizer cup of the uterine manipulator with a hand, the colpotomizer cup being formed as a single component that is sized to receive a cervix of the patient when in a nominal width configuration;
   squeezing opposite sides of the colpotomizer cup together with the hand to apply a deforming force to the colpotomizer cup, thereby adjusting the colpotomizer cup from the nominal width configuration to a reduced width folded configuration;
   inserting the colpotomizer cup into a vaginal canal of the patient while the colpotomizer cup is in the reduced width folded configuration;
   releasing the opposite sides of the colpotomizer cup to remove the deforming force from the colpotomizer cup, thereby allowing the colpotomizer cup to expand from the reduced width folded configuration to the nominal width configuration; and
   positioning the colpotomizer cup about the cervix of the patient while the colpotomizer cup is in the nominal width configuration.

2. The method of claim 1, wherein inserting the colpotomizer cup into the vaginal canal of the patient comprises moving the colpotomizer cup along a shaft of the uterine manipulator.

3. The method of claim 2, further comprising locking the colpotomizer cup at a predetermined location along the shaft.

4. The method of claim 1, further comprising advancing the colpotomizer cup within the vaginal canal to the cervix of the patient while the colpotomizer cup is in the reduced width folded configuration.

5. The method of claim 1, wherein applying the deforming force to the colpotomizer cup comprises squeezing the colpotomizer cup into the reduced width folded configuration.

6. The method of claim 5, wherein removing the deforming force from the colpotomizer cup comprises releasing the colpotomizer cup from the reduced width folded configuration.

7. The method of claim 1, wherein applying the deforming force to the colpotomizer cup comprises collapsing the colpotomizer cup into the reduced width folded configuration.

8. The method of claim 1, wherein inserting the colpotomizer cup into the vaginal canal comprises inserting the colpotomizer cup into a vaginal entryway of the patient.

9. The method of claim 1, wherein the colpotomizer cup comprises polyurethane.

10. The method of claim 1, wherein one or more materials from which the colpotomizer cup is formed have an elastic modulus in a range of about 5.5 MPa to about 171 MPa.

11. The method of claim 1, wherein one or more materials from which the colpotomizer cup is formed have a hardness in a range of 85 Shore A to 100 Shore A.

12. The method of claim 1, wherein a wall thickness of the colpotomizer cup is in a range of about 0.2 cm to about 0.7 cm.

13. The method of claim 12, wherein one or more materials from which the colpotomizer cup is formed have an elastic modulus in a range of about 5.5 MPa to about 171 MPa and a hardness in a range of 85 Shore A to 100 Shore A.

14. The method of claim 1, wherein the colpotomizer cup has a maximum internal diameter of about 2.5 cm, about 3.0 cm, about 3.5 cm, or about 4.0 cm.

15. The method of claim 1, further comprising visualizing the cervix within the colpotomizer cup through one or more of a plurality of viewing windows of the colpotomizer cup.

16. The method of claim 15, wherein the plurality of viewing windows extends about a majority of a circumference of the colpotomizer cup.

17. The method of claim 15, wherein the colpotomizer cup comprises polyurethane, and wherein a material formulation of the colpotomizer cup, together with a configuration provided by the plurality of viewing windows, enables the colpotomizer cup to fold upon itself into the reduced width folded configuration.

18. The method of claim 1, wherein the reduced width folded configuration has an oblong cross-sectional shape.

19. The method of claim 1, further comprising:
   inserting a shaft of the uterine manipulator through the cervix to position a closed distal end of the shaft at a fundus of the uterus, the shaft carrying a colpotomizer assembly that comprises the colpotomizer cup; and
   moving the colpotomizer assembly distally along the shaft to locate the colpotomizer cup at the cervix.

* * * * *